(12) United States Patent
Bachmaier et al.

(10) Patent No.: US 11,723,645 B2
(45) Date of Patent: Aug. 15, 2023

(54) SURGICAL FIXATION SYSTEMS AND METHODS

(71) Applicant: ARTHREX, INC., Naples, FL (US)

(72) Inventors: Samuel Bachmaier, Mauern (DE); Coen Wijdicks, Munich (DE)

(73) Assignee: ARTHREX, INC., Naples, FL (US)

( * ) Notice: Subject to any disclaimer, the term of this patent is extended or adjusted under 35 U.S.C. 154(b) by 867 days.

(21) Appl. No.: 16/491,049

(22) PCT Filed: Mar. 13, 2018

(86) PCT No.: PCT/US2018/022190
§ 371 (c)(1),
(2) Date: Sep. 4, 2019

(87) PCT Pub. No.: WO2018/169961
PCT Pub. Date: Sep. 20, 2018

(65) Prior Publication Data
US 2020/0015804 A1    Jan. 16, 2020

Related U.S. Application Data

(60) Provisional application No. 62/470,522, filed on Mar. 13, 2017.

(51) Int. Cl.
*A61B 17/04* (2006.01)
(52) U.S. Cl.
CPC .. *A61B 17/0401* (2013.01); *A61B 2017/0404* (2013.01)

(58) Field of Classification Search
CPC ........ A61B 17/0401; A61B 2017/0409; A61B 2017/06185; A61B 2017/06166; A61B 2017/0414; A61B 2017/0404
See application file for complete search history.

(56) References Cited

U.S. PATENT DOCUMENTS

| | | | |
|---|---|---|---|
| 5,769,894 A | 6/1998 | Ferragamo | |
| 8,795,298 B2 | 8/2014 | Hernlund et al. | |
| 8,864,797 B2 | 10/2014 | Justin et al. | |
| 8,926,662 B2 | 1/2015 | Perriello et al. | |
| 9,192,368 B2 | 11/2015 | Perriello et al. | |
| 9,561,027 B2 | 2/2017 | Perriello et al. | |
| 9,700,403 B2 | 7/2017 | Kam et al. | |
| 2006/0190041 A1 | 8/2006 | Fallin et al. | |
| 2010/0256677 A1* | 10/2010 | Albertorio | A61F 2/0811 606/232 |

(Continued)

FOREIGN PATENT DOCUMENTS

| | | |
|---|---|---|
| EP | 2238944 A2 | 10/2010 |
| JP | 2015-507952 A | 3/2015 |

OTHER PUBLICATIONS

International Search Report and Written Opinion of the International Searching Authority for International application No. PCT/US2018/022190 dated May 28, 2018.

(Continued)

*Primary Examiner* — Dianne Dornbusch
(74) *Attorney, Agent, or Firm* — Carlson, Gaskey & Olds, P.C.

(57) ABSTRACT

This disclosure relates to surgical fixation systems and methods. The surgical fixation systems can include a fixation device and an adjustable loop connected to the fixation device.

13 Claims, 19 Drawing Sheets

(56) References Cited

U.S. PATENT DOCUMENTS

| | | |
|---|---|---|
| 2010/0268273 A1 | 10/2010 | Albertorio et al. |
| 2010/0324676 A1 | 12/2010 | Albertorio et al. |
| 2011/0087280 A1* | 4/2011 | Albertorio ............ A61F 2/0811 606/232 |
| 2012/0065731 A1* | 3/2012 | Justin .................... A61F 2/0811 623/13.14 |
| 2012/0109194 A1 | 5/2012 | Miller et al. |
| 2012/0123474 A1* | 5/2012 | Zajac ................. A61B 17/8061 606/232 |
| 2012/0123541 A1* | 5/2012 | Albertorio ......... A61B 17/0401 606/232 |
| 2012/0290002 A1* | 11/2012 | Astorino .......... A61B 17/06166 606/232 |
| 2013/0197580 A1 | 8/2013 | Perriello et al. |
| 2013/0317544 A1* | 11/2013 | Ferguson ......... A61B 17/06166 606/228 |
| 2014/0257346 A1* | 9/2014 | Sengun .............. A61B 17/0401 606/148 |
| 2015/0039026 A1 | 2/2015 | Pasquali et al. |
| 2015/0157449 A1 | 6/2015 | Gustafson et al. |
| 2015/0196385 A1* | 7/2015 | Kam .................. A61B 17/0401 623/13.14 |
| 2016/0151060 A1 | 6/2016 | Albertorio et al. |
| 2016/0157851 A1 | 6/2016 | Spenciner |

OTHER PUBLICATIONS

JP Patent Application No. 2019-549572 dated Sep. 29, 2019 (English translation).

International Preliminary Report on Patentability for International application No. PCT/US2018/022190 dated Sep. 26, 2019.

Office communication for Application No. EP 18716030.4 dated Nov. 10, 2020.

\* cited by examiner

SURGICAL FIXATION SYSTEMS AND METHODS

CROSS REFERENCE TO RELATED APPLICATIONS

This application claims priority to U.S. Provisional Application No. 62/470,522, filed on Mar. 13, 2017, the entirety of which is incorporated by reference herein.

BACKGROUND

This disclosure relates to surgical fixation systems and methods for fixating a graft or filament within a bone tunnel.

Tissue reconstruction surgeries, such as anterior cruciate ligament (ACL) reconstructions and posterior cruciate ligament (PCL) reconstructions, typically involve drilling a tunnel through bone, positioning a substitute graft into the bone tunnel, and fixating the graft within the bone tunnel using a fixation device, such as a button, a screw, or the like.

SUMMARY

This disclosure relates to surgical fixation systems and methods. The surgical fixation systems may include a fixation device and a loop connected to the fixation device. A graft may be carried by the loop. The surgical fixation system can be used in various tissue reconstruction procedures, including but not limited to, ACL and PCL reconstructions.

A surgical fixation system according to an exemplary aspect of this disclosure may include, inter alia, a fixation device and an adjustable loop connected to the fixation device. The adjustable loop may include a first adjustable eyesplice loop that passes through and interlinks with a second adjustable eyesplice loop at an interconnection that rests over a bridge of the fixation device.

A fixation device of the surgical fixation system may be a button.

A bridge may be located between a first aperture and a second aperture of a fixation device.

The system may further include a third aperture of a fixation device which may carry a passing filament.

A first adjustable eyesplice loop may be received through a first aperture of the fixation device. A second adjustable eyesplice loop may be received through a second aperture of the fixation device.

An adjustable loop may include a first free braid strand for adjusting a first adjustable eyesplice loop. An adjustable loop may include a second free braid strand for adjusting a second adjustable eyesplice loop.

A first free braid strand may be passed through a second adjustable eyesplice loop and a second free braid strand may be passed through a first adjustable eyesplice loop. A first free braid strand may be passed through a first opening of a fixation device prior to passing through a second adjustable eyesplice loop. A second free braid strand may be passed through a second opening of a fixation device prior to passing through a first adjustable eyesplice loop.

A first free braid strand and/or a second free braid strand each may be spliced through an adjustable loop at least twice.

A fixation device may include a top surface and a bottom surface. A bridge may be countersunk from the top surface.

A first adjustable eyesplice loop, a second adjustable eyesplice loop, and free braid strands of an adjustable loop may co-operate to establish a knot stack at an interface between the adjustable loop and a fixation device.

A knot stack may rest over the bridge of a fixation device.

A surgical fixation system may include a knot stack at an interface between a fixation device and an adjustable loop.

A knot stack may be established by at least two adjustable eyesplice loops and free braid strands of a flexible strand that is used to form the at least two adjustable eyesplice loops.

A surgical method according to another exemplary aspect of this disclosure includes, inter alia, fixating a graft within a bone tunnel using a surgical fixation system that includes a fixation device and an adjustable loop connected to the fixation device. An adjustable loop includes at least two adjustable eyesplice loops that are interlinked at an interconnection located at an interface between the fixation device and the adjustable loop.

A surgical fixation system according to another exemplary aspect of this disclosure may include, inter alia, a fixation device and an adjustable loop connected to the fixation device. A fixation device may include a body that extends along a central longitudinal axis and may include a top surface and a bottom surface. At least one aperture and a suture return aperture may each extend through the body. For example, a first and second aperture may each extend through the body. A bridge may extend between a first aperture and a second aperture. An adjustable loop may be connected to at least one aperture. For example, an adjustable loop may be connected to a first aperture and a second aperture. A first free braid strand may extend from a first spliced section of an adjustable loop, and a second free braid strand may extend from a second spliced section of the adjustable loop. The first free braid strand and the second free braid strand may extend through a suture return aperture and then under a loop section of an adjustable loop that rests over the bridge to establish a locking mechanism of the surgical fixation system. In a locked position of the locking mechanism, a first free braid strand and a second free braid strand may be tensioned against an outer surface of the bridge by the loop section of an adjustable loop.

An outer surface of a bridge may be flush with the top surface of a fixation device.

The surgical fixation system may further include a longitudinal axis extending through an outer surface of the bridge. The longitudinal axis may be perpendicular to a central longitudinal axis.

The first aperture and the second aperture of a fixation device may be axially aligned and may be disposed along a central longitudinal axis. A suture return aperture may be offset from a central longitudinal axis in a direction toward a side wall of the body.

The surgical fixation system may include a bump, and the bump may be disposed laterally between the suture return aperture and the bridge.

A first free braid strand and a second free braid strand of an adjustable loop may be tensioned against a bump of a fixation device.

When in a locked position of the locking mechanism, a first free braid strand and a second free braid strand may be tensioned against the bump.

The surgical fixation system may include a bump that protrudes outwardly from the top surface at a location adjacent to a suture return aperture, and a first free braid strand and a second free braid strand of an adjustable loop may extend up and over the bump.

A surgical method according to another exemplary aspect of this disclosure may include, inter alia, fixating a graft within a bone tunnel using a surgical fixation system that includes a fixation device and an adjustable loop connected to the fixation device. The surgical method may include fixating a graft within a bone tunnel with the surgical fixation system of the previous exemplary aspects.

A surgical method according to another exemplary aspect of this disclosure may include, inter alia, fixating a graft within a bone tunnel using a surgical fixation system that may include a fixation device and an adjustable loop connected to the fixation device as discussed herein. A fixation device may include a body that extends along a central longitudinal axis and may include a top surface and a bottom surface. At least one aperture and a suture return aperture may each extend through the body. A first and second aperture may each extend through the body. A bridge may extend between a first aperture and a second aperture. An adjustable loop may be connected to at least one aperture. For example, an adjustable loop may be connected to a first aperture and a second aperture. A first free braid strand may extend from a first spliced section of an adjustable loop, and a second free braid strand may extend from a second spliced section of the adjustable loop. The first free braid strand and the second free braid strand may extend through a suture return aperture and then under a loop section of an adjustable loop that rests over the bridge to establish a locking mechanism of the surgical fixation system. In a locked position of the locking mechanism, a first free braid strand and a second free braid strand may be tensioned against an outer surface of the bridge by the loop section of an adjustable loop.

DETAILED DESCRIPTION

This disclosure relates to surgical fixation systems and methods. A surgical fixation system may include a fixation device and an adjustable loop connected to the fixation device. The loop may carry a graft. Surgical fixation systems may be used in various tissue reconstruction procedures, including but not limited to, ACL and PCL reconstructions.

Figure 1:
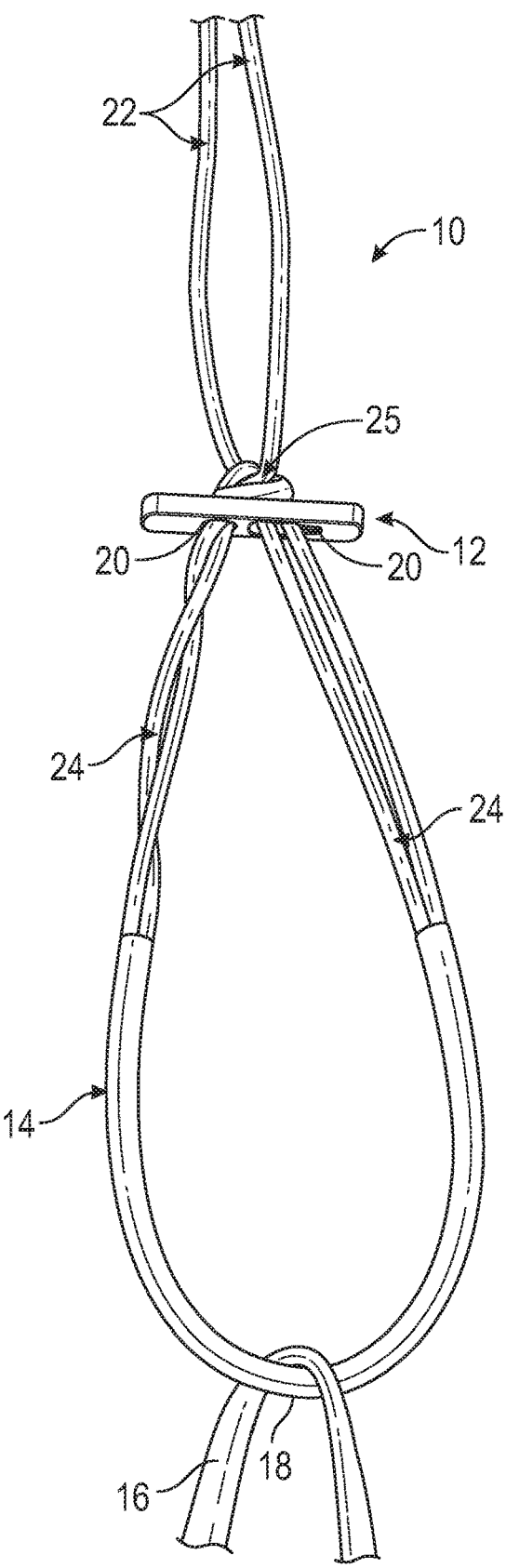
FIG. 1 illustrates a surgical fixation system for performing a tissue reconstruction procedure according to a first embodiment of this disclosure.
Figure 2:
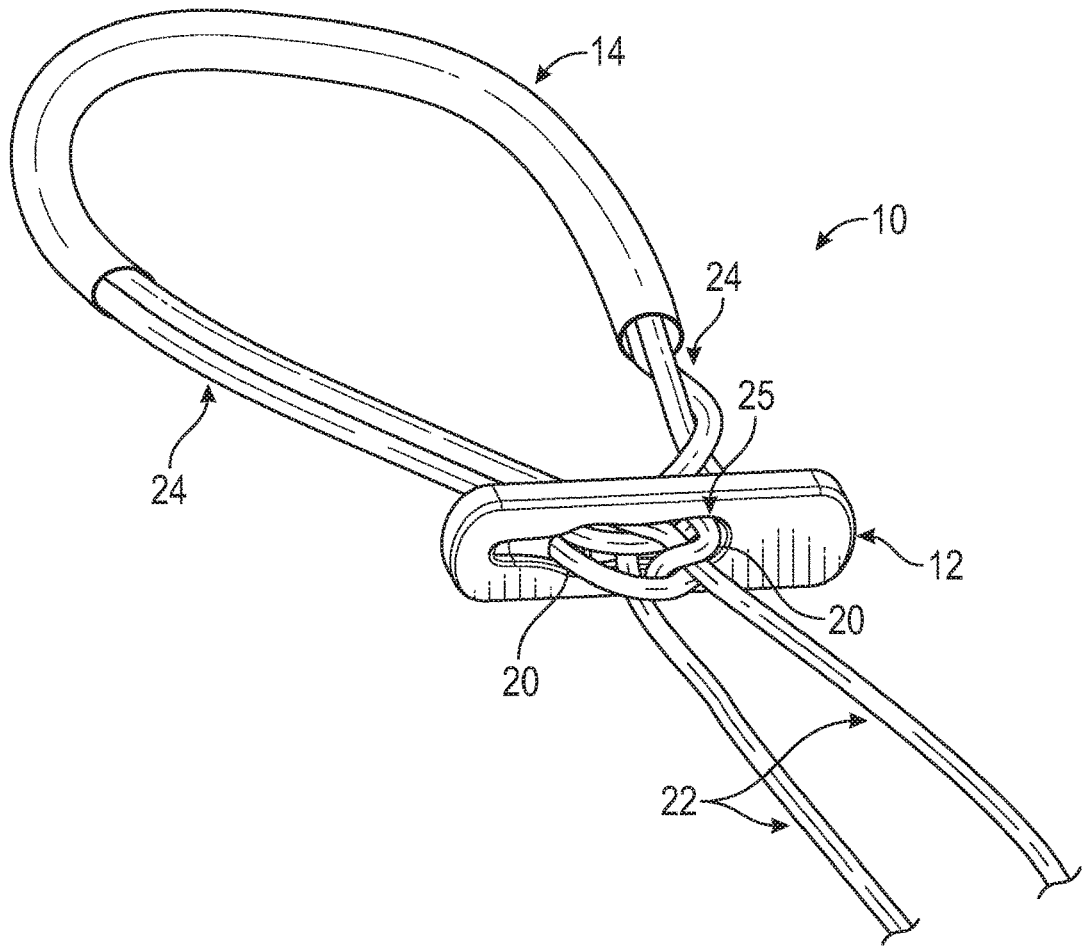
FIG. 2 is a perspective view of the surgical fixation system of FIG. 1.
Figure 3:
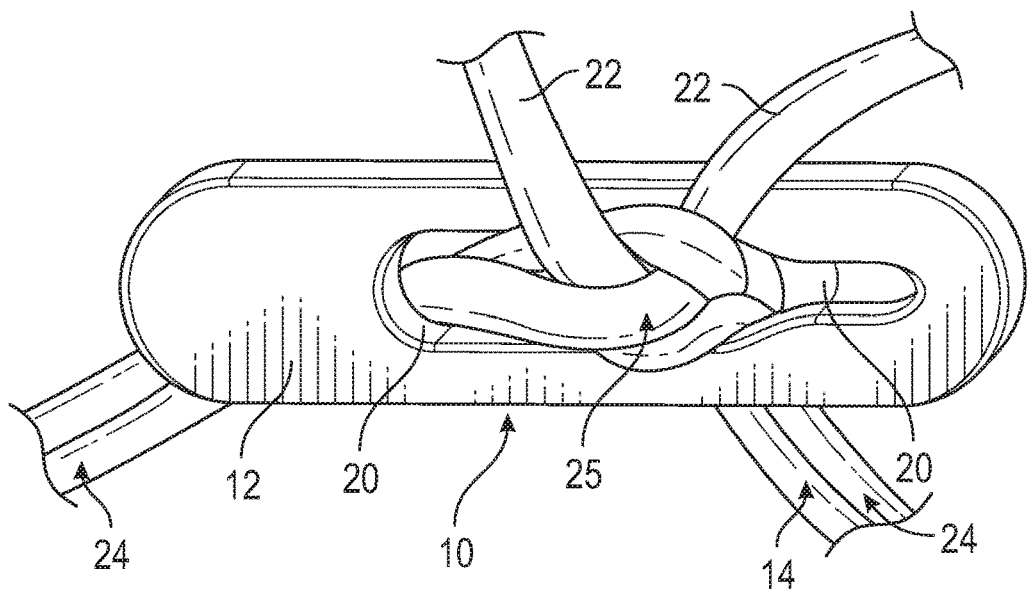
FIG. 3 is a top view of the surgical fixation system of FIG. 1.

FIGS. 1, 2, and 3 illustrate an exemplary surgical fixation system 10. The surgical fixation system 10 may be used to perform a variety of tissue reconstruction procedures. The tissue reconstruction procedures could include any procedure in which it is desirable to position a replacement graft or filament within a bone tunnel to repair torn tissue. ACL and PCL reconstructions are but two non-limiting examples of reconstruction procedures which could benefit from the use of the surgical fixation system 10 of this disclosure. The surgical fixation system 10 could additionally be used in procedures related to the ankle (e.g., syndesmosis procedures) and shoulder (e.g., acromioclavicular (AC) joint procedures).

The surgical fixation system 10 includes, in this example, a fixation device 12 and a loop 14 connected to the fixation device 12. In an embodiment, the loop 14 carries a graft 16 for fixating the graft 16 relative to bone. In another embodiment, the loop 14 carries a filament (e.g., any thread-like material such as suture, etc.) for fixating the filament relative to bone.

The fixation device 12 may provide cortical bone fixation of the graft 16 (or filament), for example, after the graft 16 has been positioned within a bone tunnel. In an embodiment, the fixation device 12 is a button. However, fixation devices having other similar configurations could also be used. The fixation device 12 may be oblong or round and may be made of either metallic or polymeric materials within the scope of this disclosure.

In another embodiment, the fixation device 12 includes one or more apertures 20 formed through the body of the fixation device 12 for receiving the loop 14. The fixation device 12 of the embodiment of FIG. 1, for example, includes two apertures 20 for connecting the loop 14 to the fixation device 12. Although not shown, the fixation device 12 could include additional apertures or openings in excess of two (see, for example, the fixation device of FIGS. 4 and 5).

In an embodiment, the loop 14 is an adjustable loop made of a flexible material, and in this example, may include an adjustable length and/or perimeter. Free braid strands 22 of the loop 14, which may also be referred to as shortening strands, may be pulled to reduce the size of the loop 14. For example, the loop 14 may be adjusted in a first direction by pulling the free braid stands 22 but is prevented from loosening in the opposite direction due to applied internal tensile forces.

The loop 14 may include one or more adjustable eyesplice loops 24, which may be formed by splicing the flexible material that is used to form the loop 14 through itself. The loop 14 may be connected to the fixation device 12 prior to completely forming the loop 14. An exemplary method of forming the loop 14 and connecting it to the fixation device 12 is discussed in greater detail below with respect to FIGS. 6-14.

The graft 16 is connected to a cradle 18 of the loop 14 (see FIG. 1). In an embodiment, the graft 16 may be looped over the cradle 18 of the loop 14. The cradle 18 is the portion of the loop 14, which in this example, is located opposite from the portion of the loop 14 that is connected to the fixation device 12. The graft 16 could include tissue, tendon, ligament, filament (e.g., suture), synthetic material, biologic material, bone, or any combinations of such materials.

In an embodiment, the adjustable eyesplice loops 24 and the free braid strands 22 cooperate to establish a knot stack 25 at the loop 14/fixation device 12 interface. The knot stack 25 rests over the fixation device 12 (e.g., just above the location where the apertures 20 are formed through the fixation device 12) and increases the strength of the connection between the loop 14 and the fixation device 12.

Figure 4:
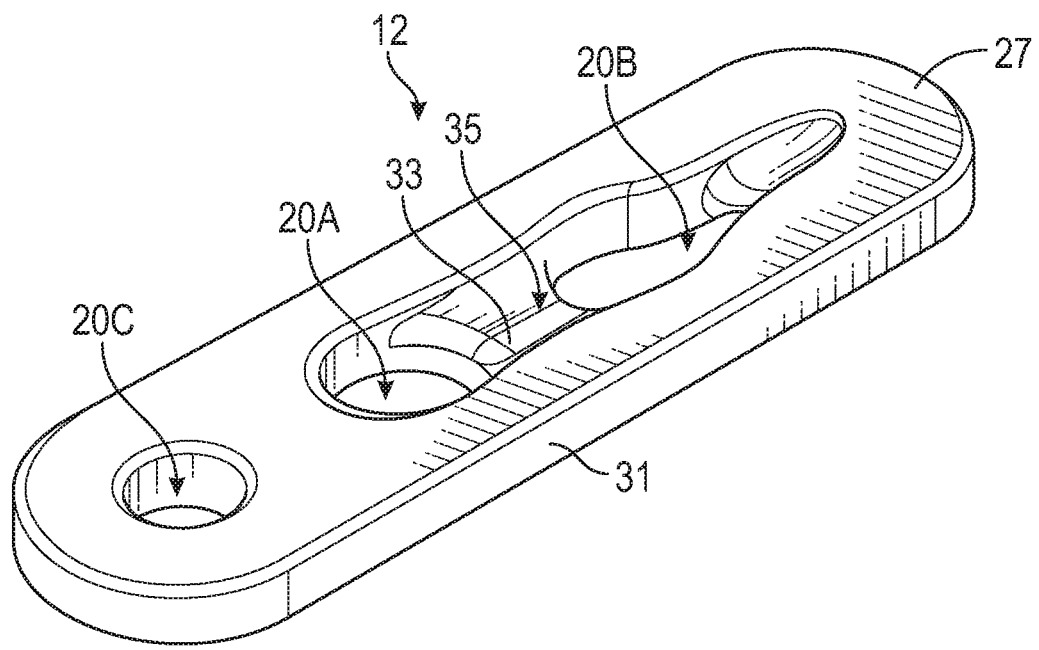
FIG. 4 is a top view of an exemplary fixation device of a surgical fixation system.
Figure 5:
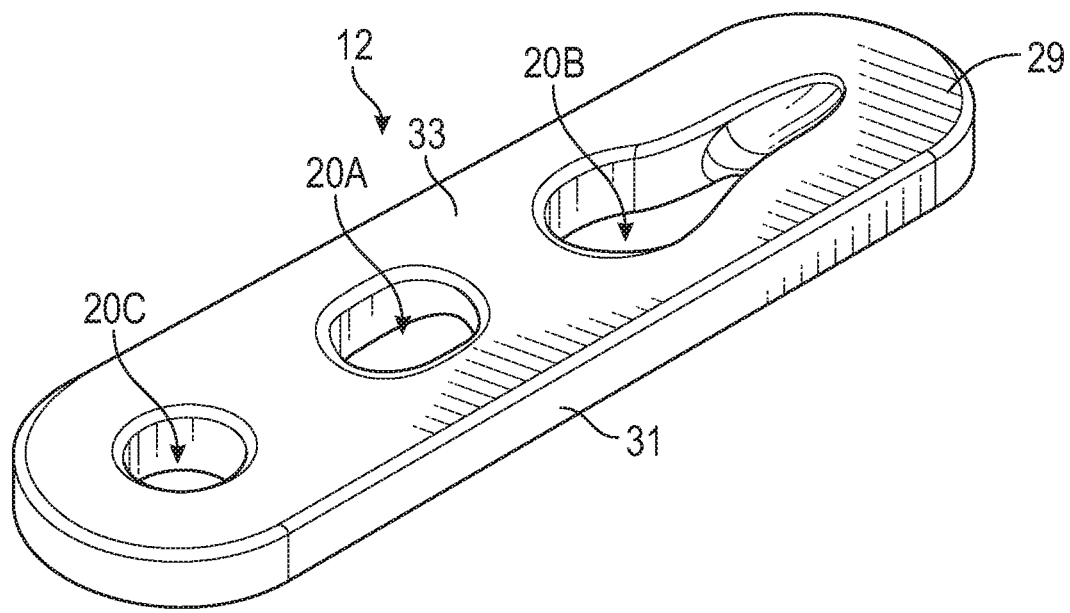
FIG. 5 is a bottom view of the fixation device of FIG. 4.

FIGS. 4 and 5 illustrate an exemplary fixation device 12 for use with a surgical fixation system, such as the surgical fixation system 10 of FIGS. 1-3, for example. The fixation device 12 may include a top surface 27 (see FIG. 4) and a bottom surface 29 (see FIG. 5). A side wall 31 extends between the top surface 27 and the bottom surface 29 to establish a body of the fixation device 12. In an embodiment, the body of the fixation device 12 is oblong shaped.

Apertures 20A, 20B, and 20C extend through both the top surface 27 and the bottom surface 29 of the fixation device 12. In an embodiment, the fixation device 12 may include three apertures. The two apertures 20A, 20B near the middle of the fixation device 12 can be used to attach the loop 14, whereas the peripheral aperture 20C can be used to carry a passing suture for passing and/or flipping the fixation device 12 relative to bone. In an embodiment, the apertures 20A and 20C are round and the aperture 20C is tear-drop shaped. Other shapes and combinations of shapes are also contemplated.

A bridge 33 separates the apertures 20A, 20B from one another and provides a surface for carrying the loop 14 of the surgical fixation system 10. The bridge 33 may be countersunk from the top surface 27 to establish a channel 35 at the top surface 27. The knot stack 25 of the loop 14 may be at least partially received within the channel 35.

The bridge 33 may not be countersunk at the bottom surface 29 (see FIG. 5) since there is no need to accommodate the knot stack 25 on that side of the fixation device 12. Thus, the bottom surface 29 of the fixation device 12 may be generally flat. Stated another way, the top surface 27 and the bottom surface 29 may be non-symmetric to one another.

Figure 6:
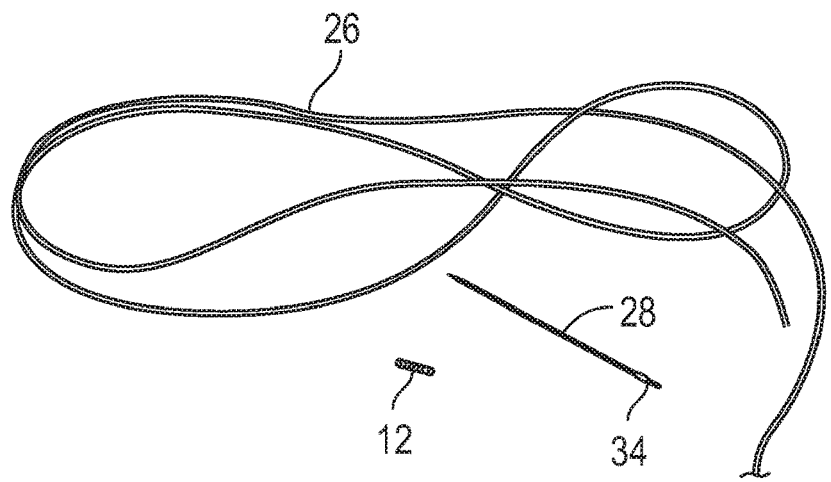
FIGS. 6, 7, 8, 9, 10, 11, 12, 13, and 14 schematically illustrate a method for forming an adjustable loop of the surgical fixation system of FIG. 1.

FIGS. 6-14 schematically illustrate an exemplary method of forming the loop 14 of the surgical fixation system 10 of FIGS. 1-3. FIG. 6 illustrates starting materials for constructing the loop 14 and attaching it to the fixation device 12. The starting materials include, for example, a flexible strand 26, such as a suture strand, a suture passing device 28, such as a needle, and the fixation device 12, such as a button.

Figure 7:
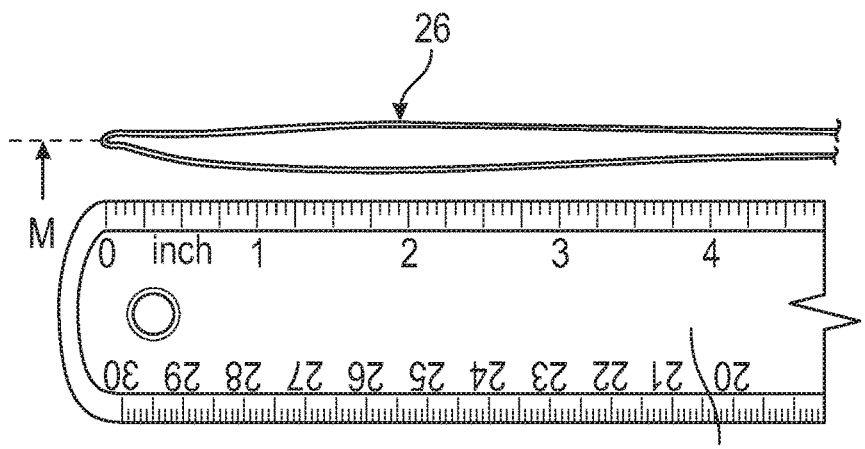

Referring next to FIG. 7, the flexible strand 26 is folded in half to create two substantially equal length and, in this example, parallel braid strands. The flexible strand 26 may be folded near its midpoint M to create the two substantially equal length and, in this example, parallel braid strands. A measuring device 30, such as a ruler, may be used to select a desired amount of the flexible strand 26 for creating a loop 14 having a desired size.

Figure 8:
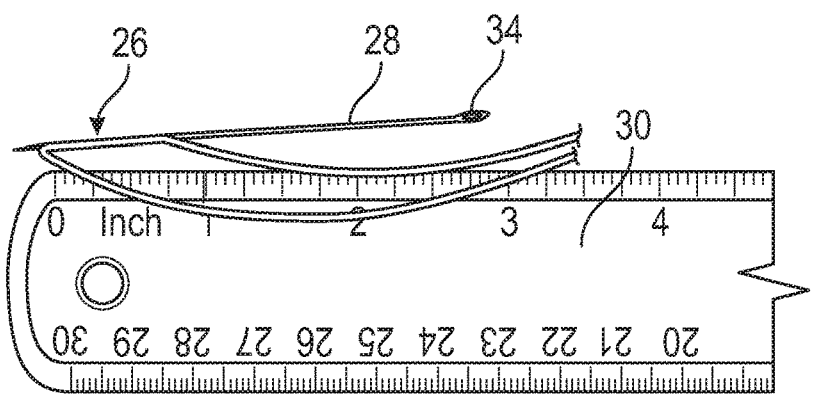
Figure 9:
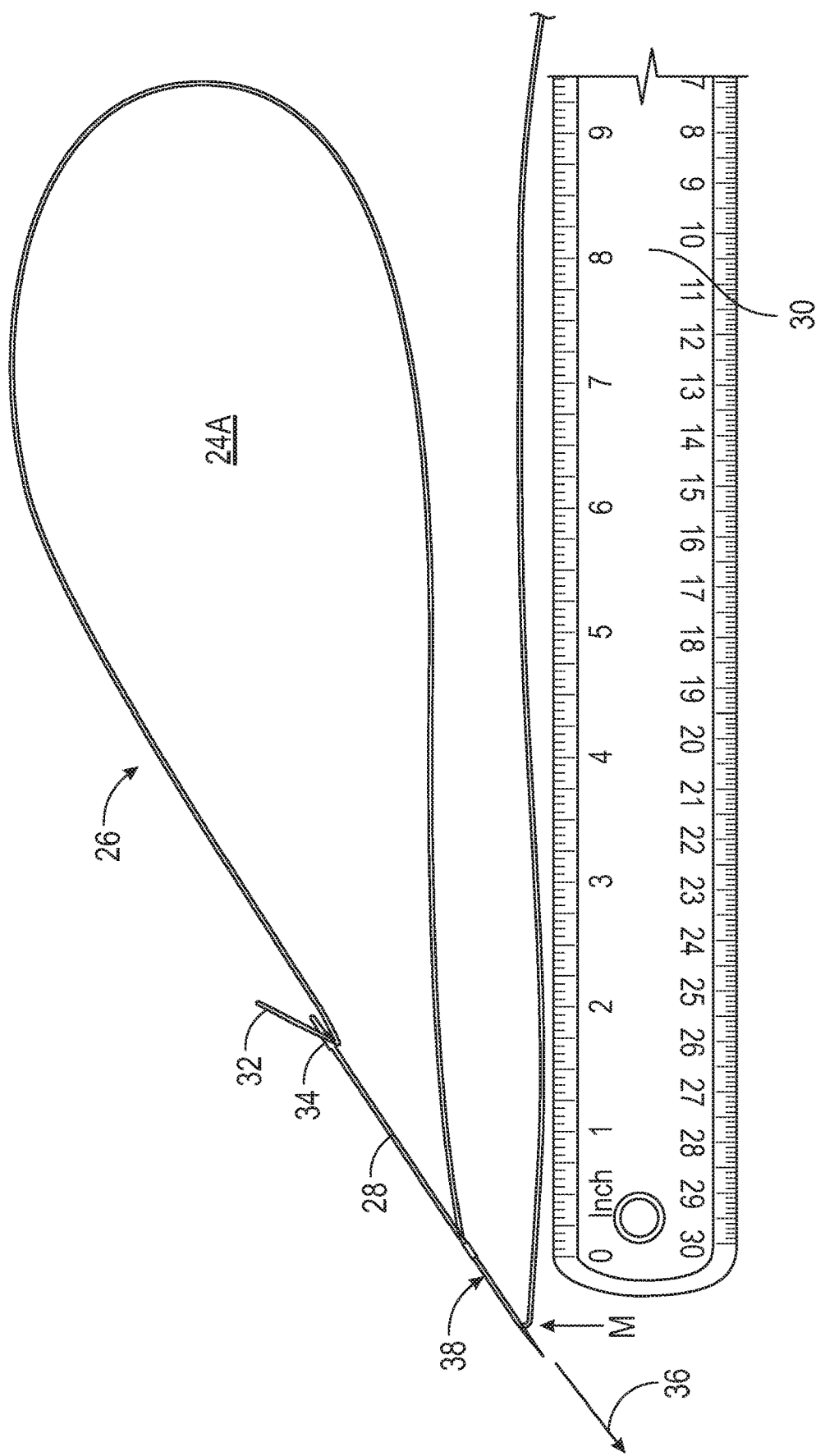

FIGS. 8 and 9 illustrate an example of the formation of a first adjustable eyesplice loop 24A of the loop 14. The first adjustable eyesplice loop 24A may be created by first passing the suture passing device 28 through the flexible strand 26 (see FIG. 8). The suture passing device 28 may be passed through the flexible strand 26 near the midpoint M where the flexible strand 26 was previously folded to mark the location where the flexible strand 26 will ultimately be spliced through itself. A first free end 32 of the flexible strand 26 may be next inserted through an eyelet 34 of the suture passing device 28 (see FIG. 9). The suture passing device 28 may then be moved (e.g., pulled) in a direction of arrow 36 to splice the first free end 32 back through the flexible strand 26 at the location where the suture passing device 28 previously passed through the flexible strand 26. This creates a first spliced section 38 in the flexible strand 26.

Figure 10:
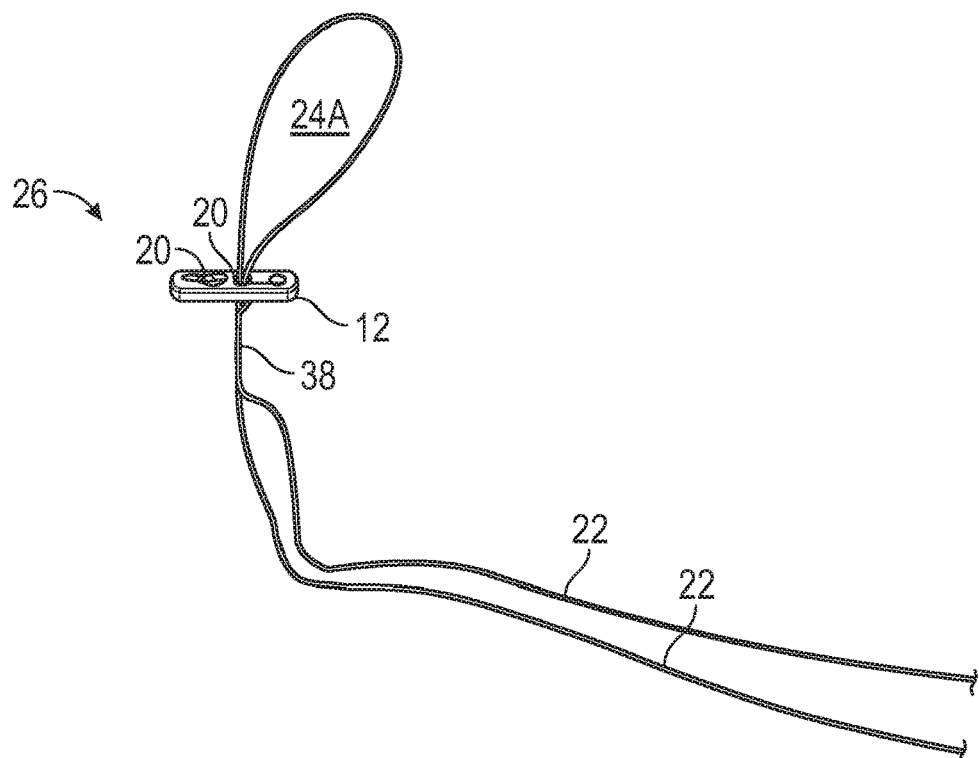

Referring now to FIG. 10, the first adjustable eyesplice loop 24A may be passed through one of the apertures 20 of the fixation device 12 to begin to connect the flexible strand 26 to the fixation device 12. The fixation device 12 may be slid until, in this example, it rests just above the first spliced section 38.

Figure 11:
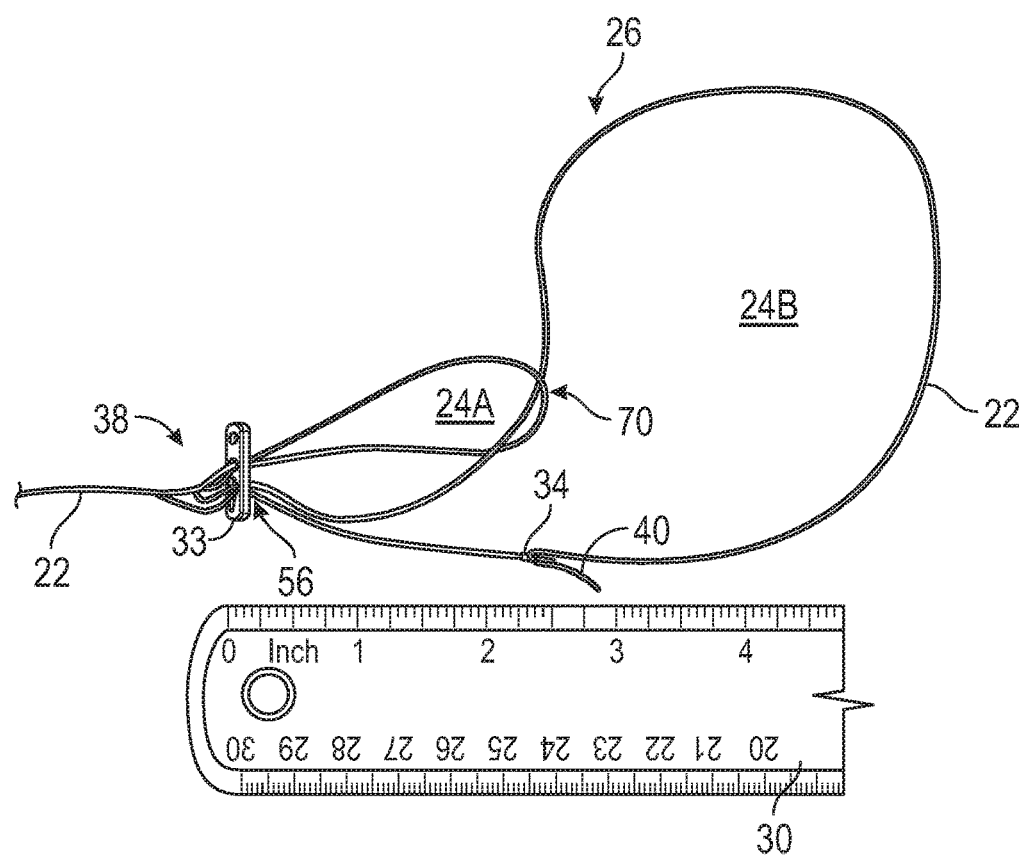

FIG. 11 illustrates the formation of a second adjustable eyesplice loop 24B of the loop 14. A second free end 40 of the flexible strand 26 may be looped through the first adjustable eyesplice loop 24A and can then be inserted through the eyelet 34 of the suture passing device 28 prior to pulling the suture passing device 28 back through the flexible strand 26. This splices the second free end 40 back through the flexible strand 26 to create a second spliced section 56. In this way, the first adjustable eyesplice loop 24A and the second adjustable eyesplice loop 24B become interlinked at an interconnection 70 that, in this example, will ultimately rest over the bridge 33 of the fixation device 12. This may also securely connect the loop 14 to the fixation device 12.

Figure 12:
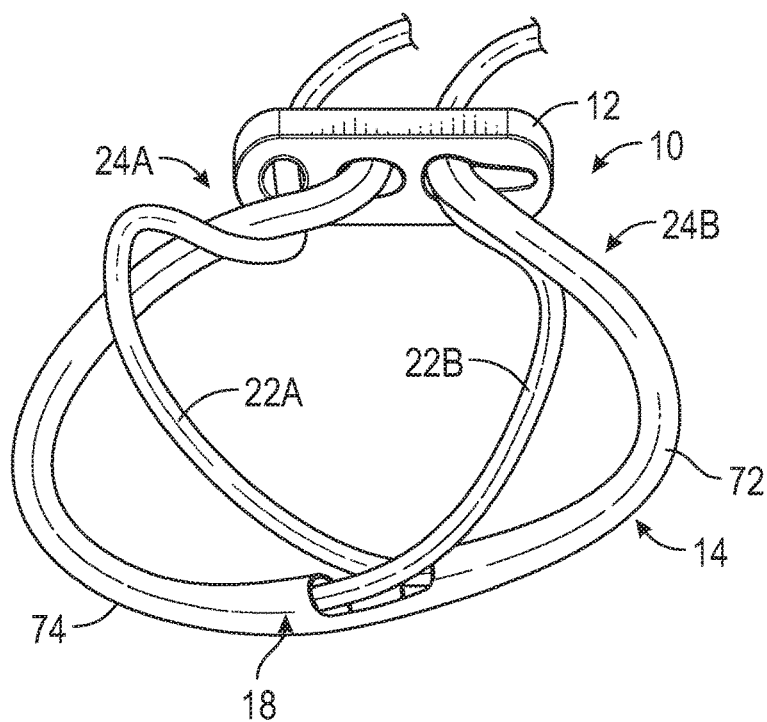
Figure 13:
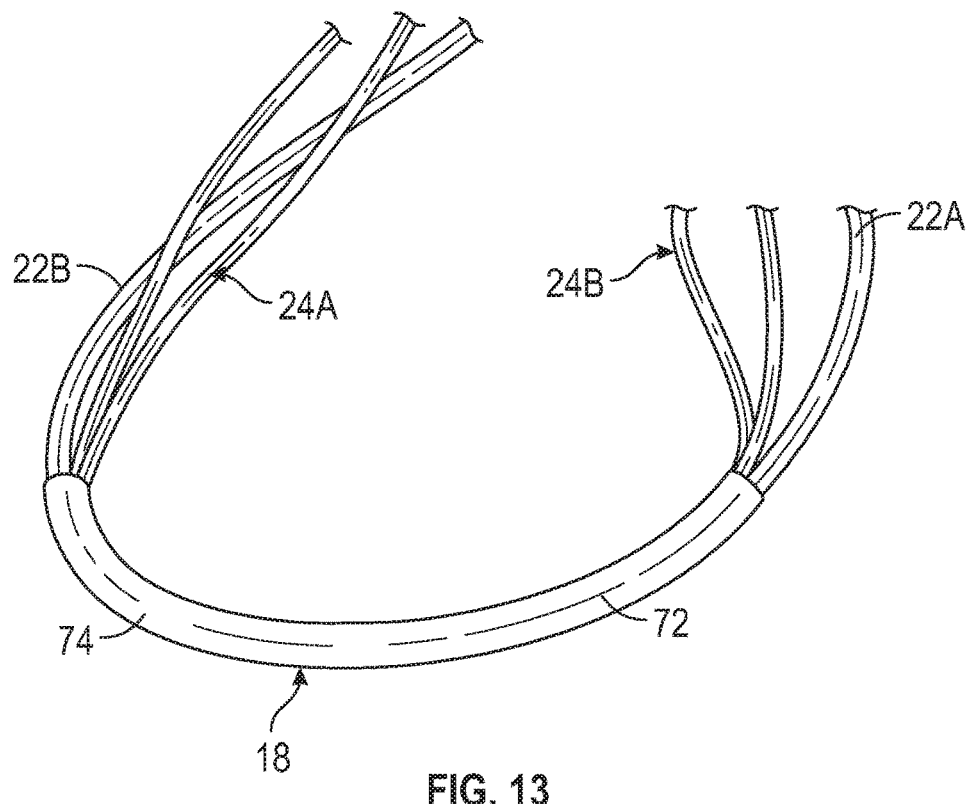

Referring now to FIGS. 12 and 13, the first adjustable eyesplice loop 24A includes a first free braid strand 22A and the second adjustable eyesplice loop 24B includes a second free braid strand 22B. The first and second free braid strands 22A, 22B may be positioned on an opposite side of the fixation device 12 from the knot stack 25. The first free braid strand 22A may be pulled back through the cradle 18 of the flexible strand 26, for example, on the right side of the construct (when looking down on the construct as shown in FIGS. 12 and 13) to create a third spliced section 72. The second free braid strand 22B may be pulled back through the cradle 18 of the flexible strand 26 on, for example, the left side of the construct to create a fourth spliced section 74.

Figure 14:
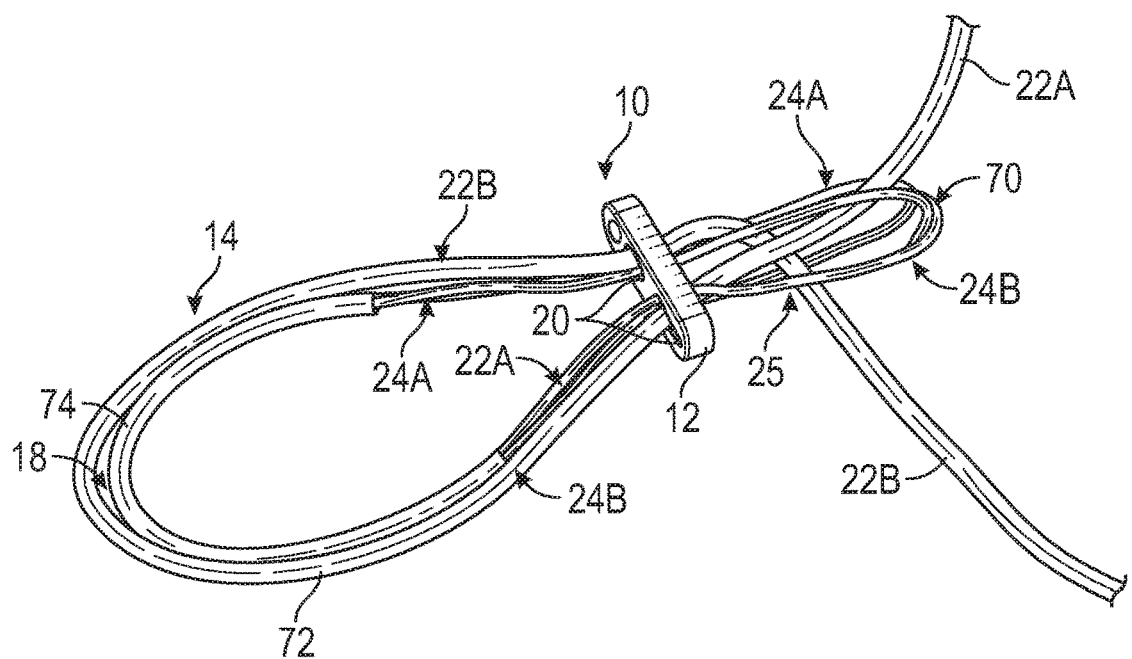

FIG. 14 illustrates the completed loop 14, which in this embodiment, includes two adjustable eyesplice loops 24A, 24B that are interlinked to one another at the interconnection 70. The fixation device 12 may be centered between the first adjustable eyesplice loop 24A and the second adjustable eyesplice loop 24B to complete the assembly procedure. The free braid strands 22A, 22B extending from the spliced sections 72, 74 may be passed back through the apertures 20 of the fixation device 12. Next, the first free braid strand 22A is passed through the first adjustable eyesplice loop 24A, and the second free braid strand 22B is passed through the second adjustable eyesplice loop 24B, thus completing the formation of the knot stack 25.

The free braid strands 22A, 22B may be pulled to constrict the size of the first and second adjustable eyesplice loops 24A, 24B, respectively and thus may change the overall size of the loop 14. The knot stack 25 may act as a first locking mechanism at the loop 14/fixation device 12 interface. The spliced sections 72, 74 may act as additional locking mechanisms, in this example, at the distal graft 16/loop 14 interface.

Figure 15:
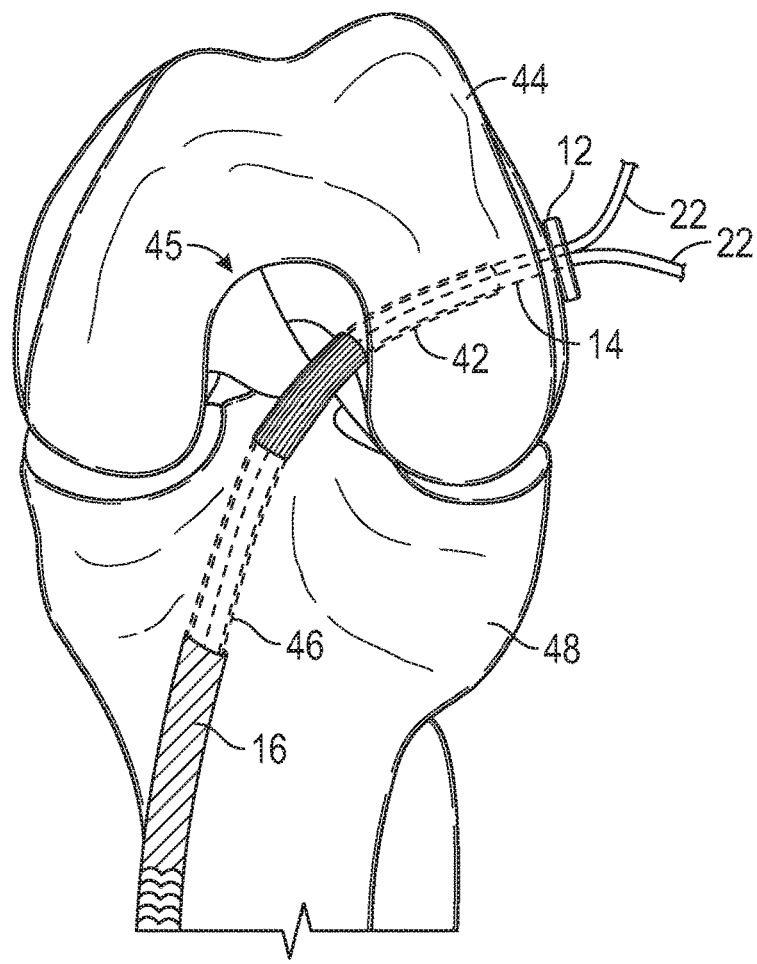
FIG. 15 schematically illustrates an exemplary use of the surgical fixation system of FIG. 1 as part of a tissue reconstruction procedure.

FIG. 15 illustrates an exemplary surgical use of the surgical fixation system 10 of FIGS. 1-3 during a tissue reconstruction procedure, such as an ACL reconstruction procedure. However, it should be understood that this disclosure is not limited to ACL reconstruction procedures, and the surgical fixation system 10 could be used in a variety of reconstruction procedures within the scope of this disclosure.

The surgical fixation system 10 may be implanted within a joint 45 (e.g., a knee joint) to repair a torn tissue (e.g., a torn ACL). Prior to positioning the surgical fixation system 10 within the joint 45, a first bone tunnel 42 (e.g., a socket) is formed in a first bone 44 (e.g., a femur) and a second bone tunnel 46 (e.g., a passage) is formed in a second bone 48 (e.g., a tibia). The first bone tunnel 42 and the second bone tunnel 46 may be formed using known drilling techniques to establish voids within the first and second bones 44, 48 for accommodating the surgical fixation system 10.

In an exemplary embodiment, the surgical fixation system 10 is implanted by passing the fixation device 12 through the first bone tunnel 42 and the second bone tunnel 46. The fixation device 12 may be pulled through the first and second bone tunnels 42, 46 using a passing suture (not shown) and self-flips onto the cortex of the first bone 44 once tension is released on the passing suture.

After passing and flipping the fixation device 12, the loop 14 is positioned within the first bone tunnel 42. The free braid strands 22 may be pulled to adjust the size of the loop 14 and to aid the positioning of the loop 14 within the first bone tunnel 42. The loop 14 suspends the graft 16 within portions of the first bone tunnel 42 and the second bone tunnel 46.

Fixation of the graft 16 to the second bone 48 can be achieved in a variety of ways. For example, the graft 16 may be fixated within the second bone tunnel 46 using an interference screw, a suture anchor, or an additional surgical fixation system that includes a second fixation device and a second loop.

EXAMPLES

Example 1

Elongation Testing

Figure 16:
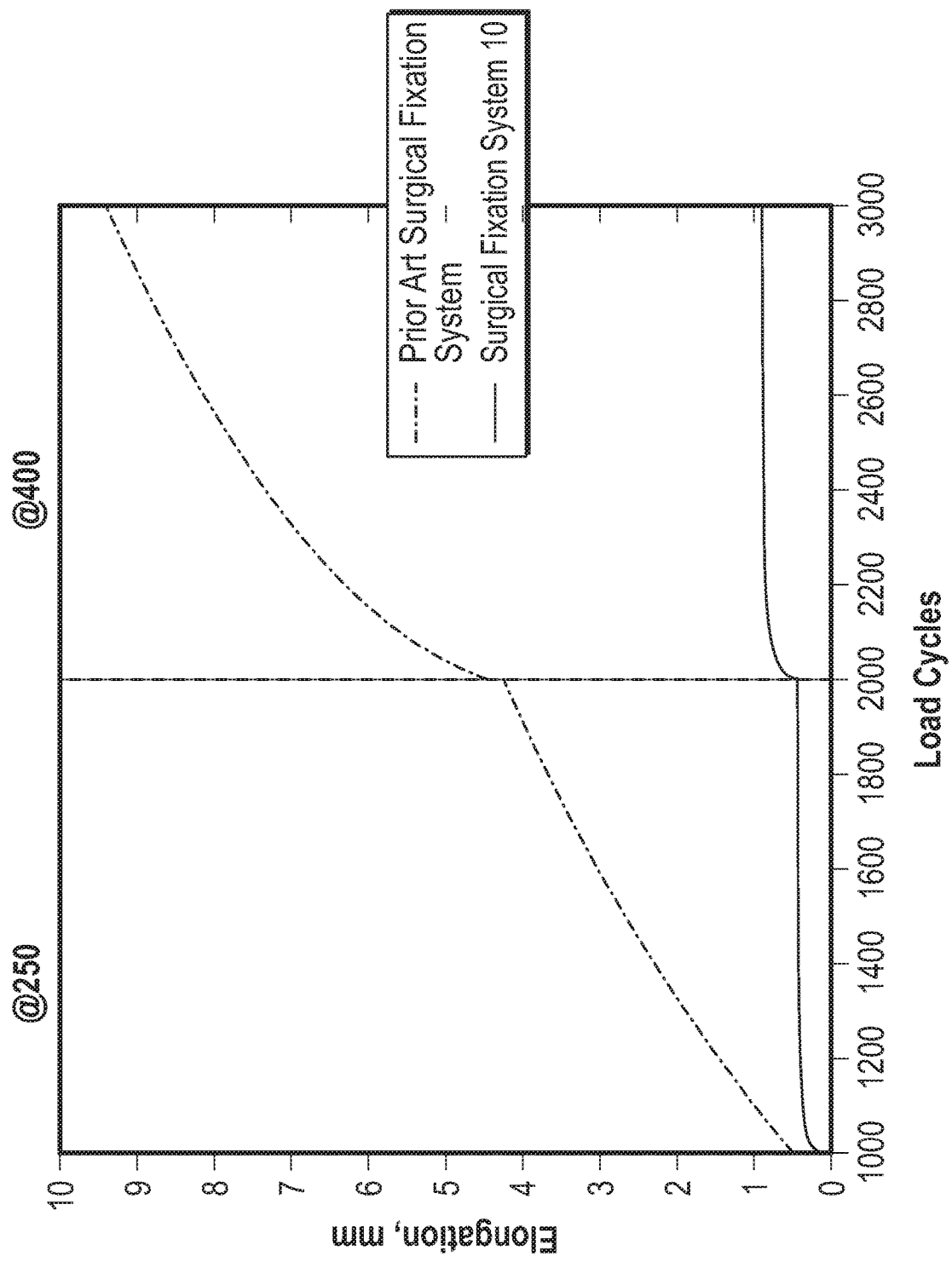
FIG. 16 is a graph illustrating elongation behavior of a sample surgical fixation system.

The surgical fixation system 10 of FIGS. 1-3 was tested against a prior art surgical fixation system using a force controlled cyclic loading procedure. Elongation was measured over multiple load cycles for each system. The results of this testing are shown in the plots of FIG. 16.

Example 2

Displacement Testing

Figure 17:
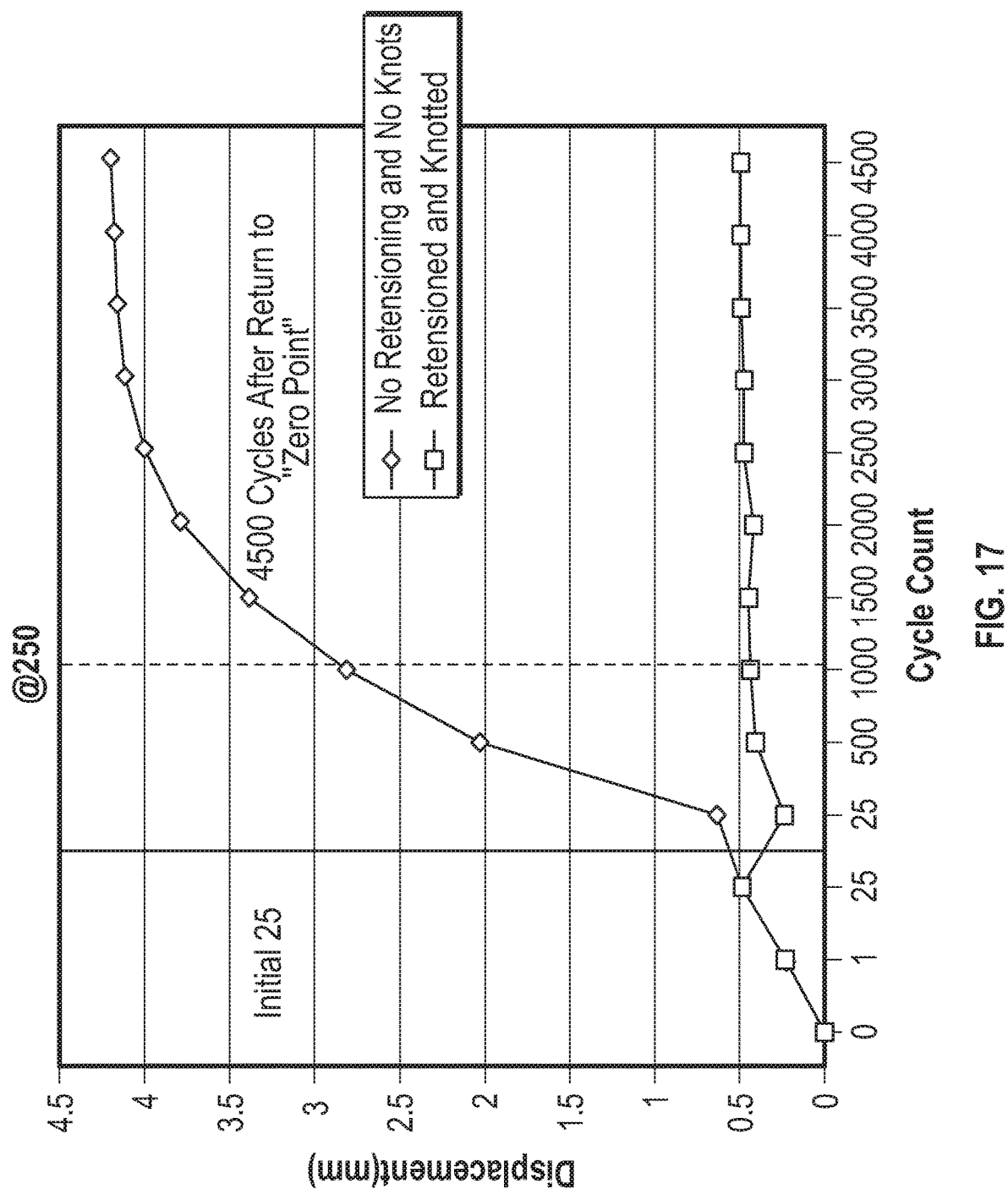
FIG. 17 is a graph illustrating displacement behavior of a sample surgical fixation system.

The surgical fixation system 10 of FIGS. 1-3 was tested using a displacement controlled cyclic loading procedure. Displacement was measured over multiple load cycles. The results of this testing are shown in the plots of FIG. 17 (with and without retensioning).

The surgical fixation systems of this disclosure provide an adjustable fixation system for reinforcing and augmenting graft fixation within a bone tunnel. The surgical fixations systems provide the following benefits over predicate devices:

independent locking mechanisms;
higher failure loads (~1400N) than most predicate devices
less cyclic displacement (~0.9 mm) than most predicate devices after 3000 cycles at unloading/loading transition zone (1k cycles), 10-250N (1k cyc), and 10-400N (1k cyc) load blocks;
downward force of the graft compresses the knot stack into the channel of the fixation device and secures the shortening strands;
knotless locking function on fixation device side via knot stack;
single loop tensioning (one hand pull) mechanism which reduces suture breakage during single tensioning system, and less confusion with suture management;
ability to use in various configurations (e.g., ABS, BTB, PCL);
could be applied to other joints such as the ankle or AC joint;
ability to implement various additional suture configurations.

Figure 18:
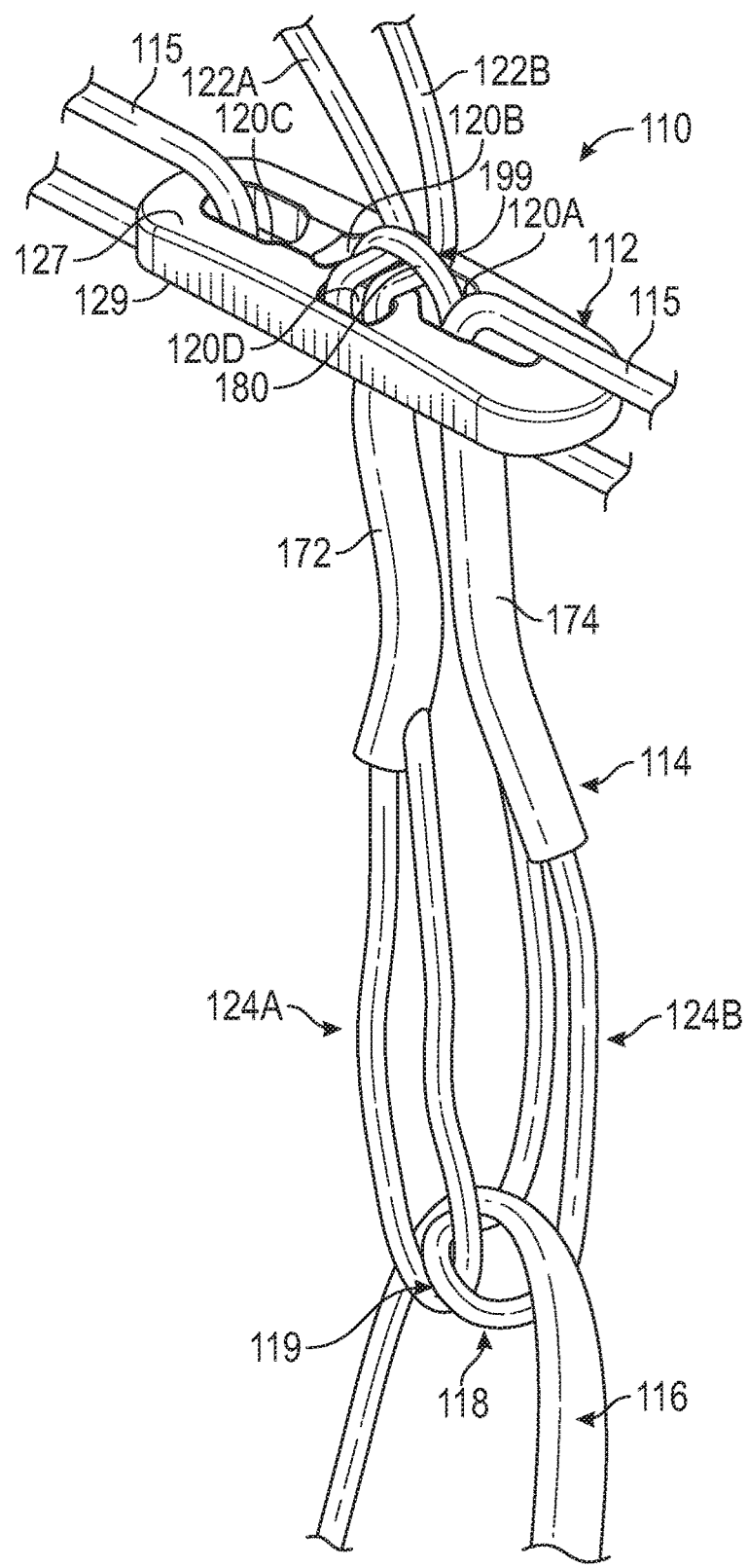
FIG. 18 illustrates a surgical fixation system for performing a tissue reconstruction procedure according to a second embodiment of this disclosure.
Figure 19:
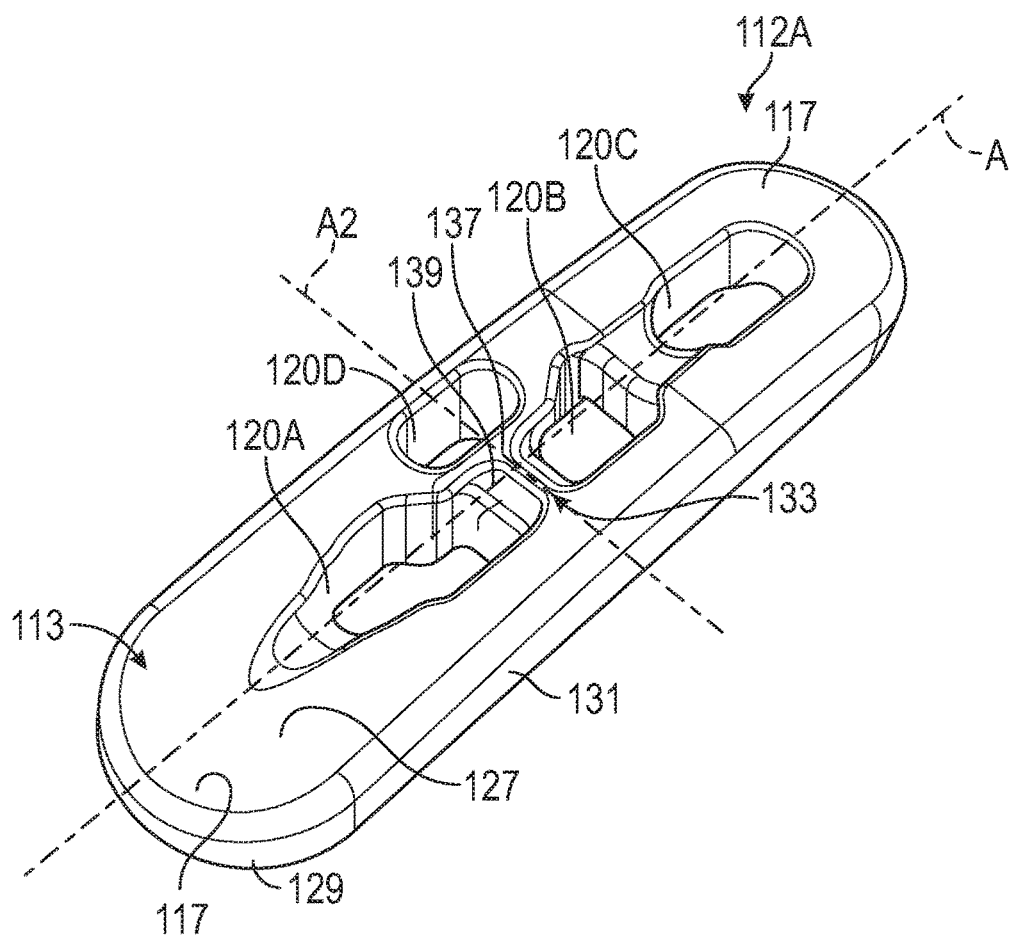
FIG. 19 illustrates an exemplary fixation device that can be used with the surgical fixation system of FIG. 18.
Figure 20:
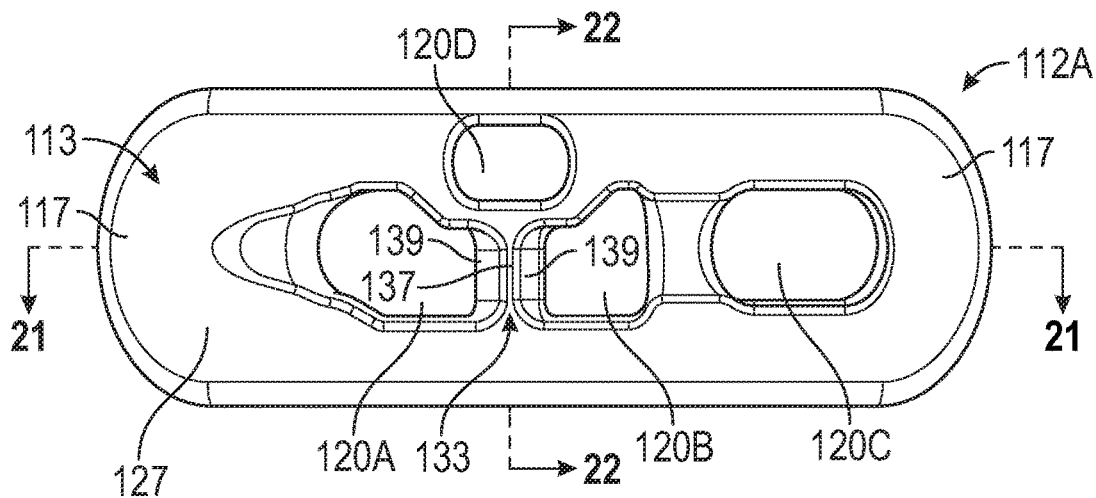
FIG. 20 is a top view of the fixation device of FIG. 19.
Figure 21:
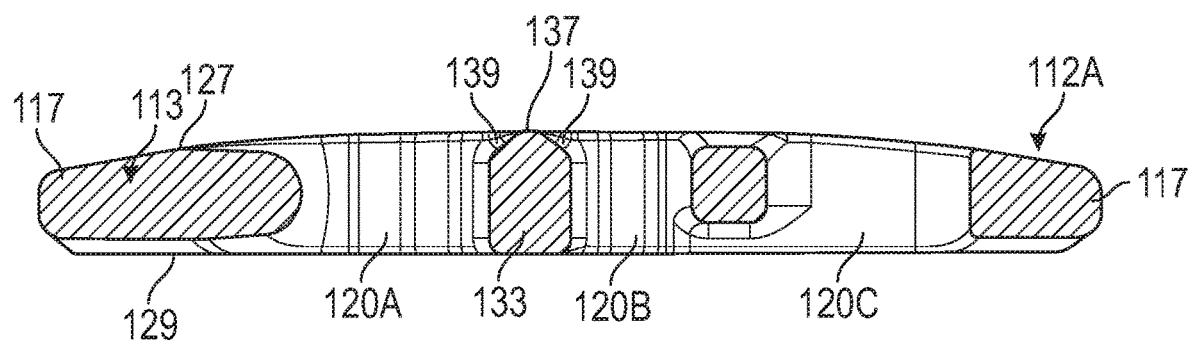
FIG. 21 is a cross-sectional view through section 21-21 of FIG. 20.
Figure 22:
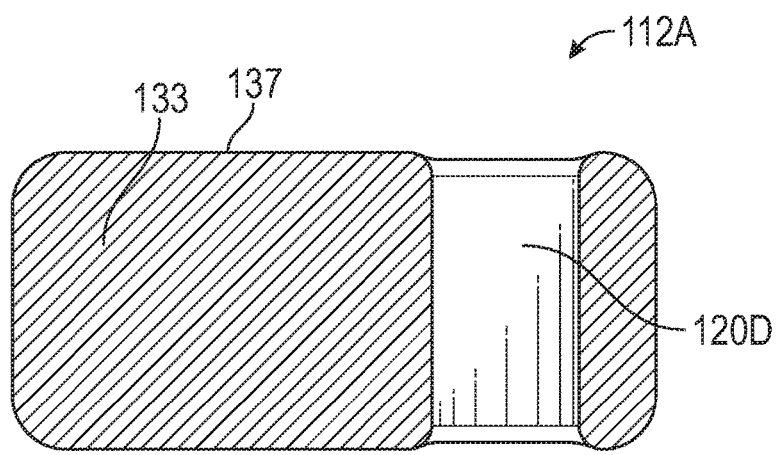
FIG. 22 is a cross-sectional view through section 22-22 of FIG. 20.

FIG. 18 illustrates another exemplary surgical fixation system 110. The surgical fixation system 110 may be used to perform a variety of tissue reconstruction procedures.

The surgical fixation system 110, in this example, includes a fixation device 112 and a loop 114 connected to the fixation device 112. In an embodiment, the loop 114 carries a graft 116, for example, for fixating the graft 116 relative to bone.

The fixation device 112 may provide cortical bone fixation of the graft 116 (or filament), for example, after the graft 116 has been positioned within a bone tunnel. In an embodiment, the fixation device 112 is a button. However, fixation devices having other similar configurations could also be used. The fixation device 112 may be oblong or round and may be made of either metallic or polymeric materials within the scope of this disclosure. Two exemplary fixation device designs are further described below (see FIGS. 19-22 and 25-28, respectively).

In another embodiment, the fixation device 112 includes a plurality of apertures 120 formed through the body of the fixation device 112 for receiving the loop 114. Some of the apertures 120 may additionally carry one or more filaments 115, such as sutures, that can be used for passing the fixation device 112 through a bone tunnel and and/or for flipping the fixation device 112 relative to bone after exiting from the bone tunnel.

In an embodiment, the loop 114 is an adjustable loop made of a flexible material, and this example, includes an adjustable length and/or perimeter. Free braid strands 122A, 122B of the loop 114, which may also be referred to as shortening strands, may be pulled to reduce the size of the loop 114. For example, the loop 114 may be adjusted in a first direction by pulling the free braid stands 122A, 122B but is prevented from loosening in the opposite direction due to applied internal tensile forces.

The loop 114 may include one or more adjustable eye-splice loops 124A, 124B which may be formed by splicing the flexible material that may be used to form the loop 114 through itself. The loop 114 may be connected to the fixation device 112 prior to completely forming the loop 114.

The graft 116 is connected to a cradle 118 of the loop 114. In an embodiment, the graft 116 may be looped over the cradle 118 of the loop 114. The cradle 118 in this embodiment is established by an interconnection 119 of the eyesplice loops 124A, 124B. The graft 116 could include tissue, tendon, ligament, filament (e.g., suture), synthetic material, biologic material, bone, or any combinations of such materials.

In an embodiment, the loop 114 and the fixation device 112 may cooperate to establish a locking mechanism 199 of the surgical fixation system 110. The locking mechanism 199 locks the size and position of the loop 114 relative to the fixation device 112, thereby increasing the strength at the loop 114/fixation device 112 interface. The locking mechanism 199 may be a byproduct of a combination of features of the loop 114 and the fixation device 112. The locking mechanism 199 is discussed in greater detail below with reference to different designs of the fixation device 112.

FIGS. 19-22 illustrate an exemplary fixation device 112A for use with a surgical fixation system, such as the surgical fixation system 110 of FIG. 18, for example. The fixation device 112A includes a body 113 that extends along a central longitudinal axis A between opposing end portions 117. In an embodiment, the body 113 of the fixation device 112A is oblong shaped.

The body 113 includes a top surface 127 and a bottom surface 129 that each extend between the opposing end portions 117. A side wall 131 extends between the top surface 127 and the bottom surface 129. Together, the top surface 127, the bottom surface 129, and the side wall 131 establish the body 113 of the fixation device 112A.

In an embodiment, the top surface 127 is a convex surface that curves in a direction away from the bottom surface 129. In another embodiment, the bottom surface 129 is a flat surface.

In this example, a first aperture 120A, a second aperture 120B, a third aperture 120C, and a fourth aperture 120D are formed through the body 113 of the fixation device 112A and extend through both the top surface 127 and the bottom surface 129. In an embodiment, the first aperture 120A, the second aperture 120B, and the third aperture 120C may be axially aligned and are disposed along the central longitudinal axis A, and the fourth aperture 120D may be offset from the central longitudinal axis A, for example, in a direction toward the side wall 131. In an embodiment, the first aperture 120A and the second aperture 120B include irregular shapes, and the third aperture 120C and the fourth aperture 120D are oval shaped. However, the sizes and shapes of the apertures are not intended to limit this disclosure.

The first aperture 120A and the second aperture 120B may be configured and arranged to receive the loop 114 of the surgical fixation system 110. A bridge 133 may separate the first and second apertures 120A, 120B from one another and may provide a surface for carrying the loop 14 of the surgical fixation system 10. The bridge 133 may include an outer surface 137 that is flush to the top surface 127 of the fixation device 112A (i.e., the outer surface 137 is not countersunk relative to the top surface 127) and, for example, a pair of angled surfaces 139 that extend transversely from the bridge 133 in a direction toward the bottom surface 129 of the fixation device 112A. In an embodiment, the outer surface 137 of the bridge 133 extends along a longitudinal axis A2 that is, for example, generally perpendicular to the central longitudinal axis A of the body 113 (see FIG. 19).

The third aperture 120C may be used to carry one or more filaments 115 for passing the fixation device 112A through a bone tunnel and/or for flipping the fixation device 112A relative to bone after exiting from the bone tunnel. The third aperture 120C may be the aperture that is closest to one of the opposing end portions 117 of the fixation device 112A.

The fourth aperture 120D may be utilized as a suture return aperture for receiving the free braid strands 122A, 122B of the loop 114. The fourth aperture 120D may be located adjacent to the first and second apertures 120A, 120B. In an embodiment, the longitudinal axis A2 extending through the outer surface 137 of the bridge 133 may intersect the fourth aperture 120D (see, e.g., FIG. 19).

With reference now to FIGS. 18-22, the fixation device 112A and the loop 114 may be configured to establish the locking mechanism 199 of the surgical fixation system 110. In an embodiment, a first free braid strand 122A extends from a first spliced section 172 of the loop 114, and a second free braid strand 122B extends from a second spliced section 174 of the loop 114. The first free braid strand 122A and the second free braid strand 122B may be passed upwardly through, in this example, the fourth aperture 120D (i.e., in a direction that extends from the bottom surface 129 toward the top surface 127 of the fixation device 112A) and may then be passed beneath a loop section 180 of the loop 114 that may, for example, rest over the bridge 133 (i.e., between the loop section 180 and the bridge 133) to establish the locking mechanism 199.

Figure 23A:
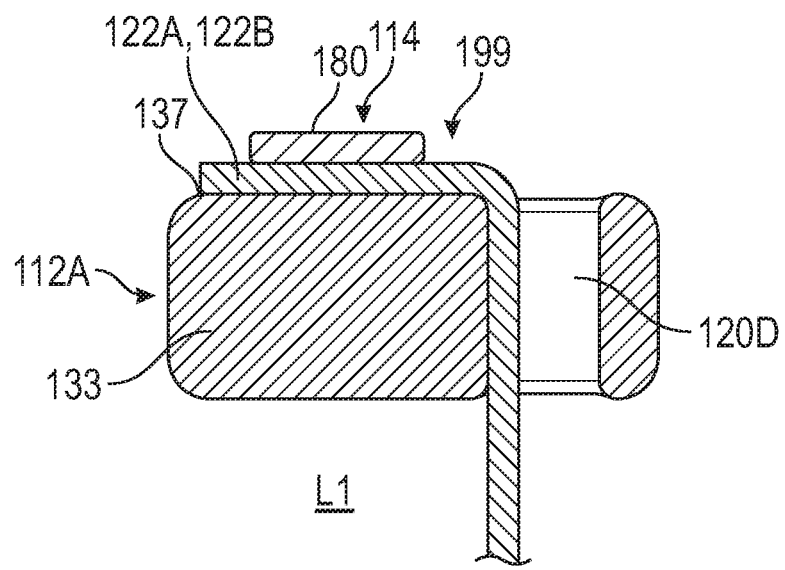
FIGS. 23A and 23B illustrate a locked position of a locking mechanism of a surgical fixation system.
Figure 23B:
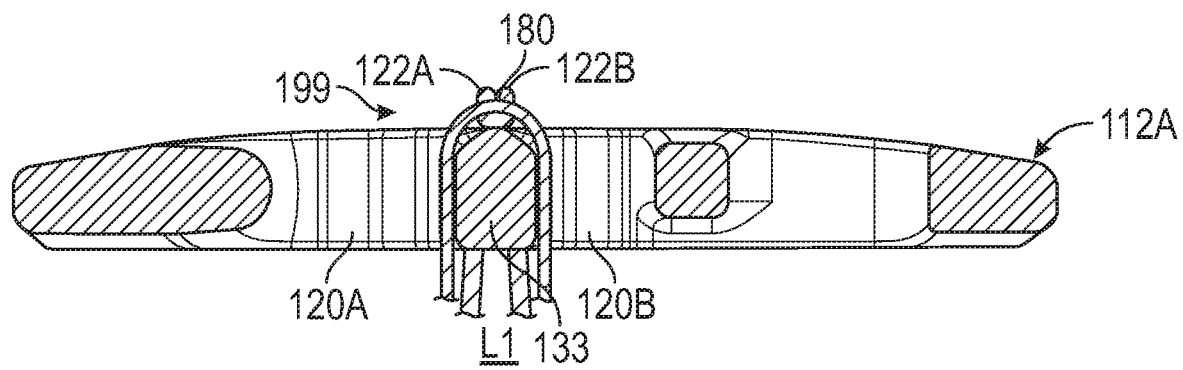

FIGS. 23A and 23B illustrate a locked position L1 of the locking mechanism 199 that is established by the loop 114 and the fixation device 112A. In the locked position L1, the free braid strands 122A and 122B are held in tension directly against the outer surface 137 of the bridge 133 by the loop section 180 of the loop 114. This tension may be created, for example, by tensioning an opposite section of the loop 114 (i.e., for example, the cradle 118 that carries the graft 116). The free braid strands 122A, 122B may therefore be held against the type of movement that is necessary for constricting the size of the first and second adjustable eyesplice loops 124A, 124B of the loop 114.

Figure 24A:
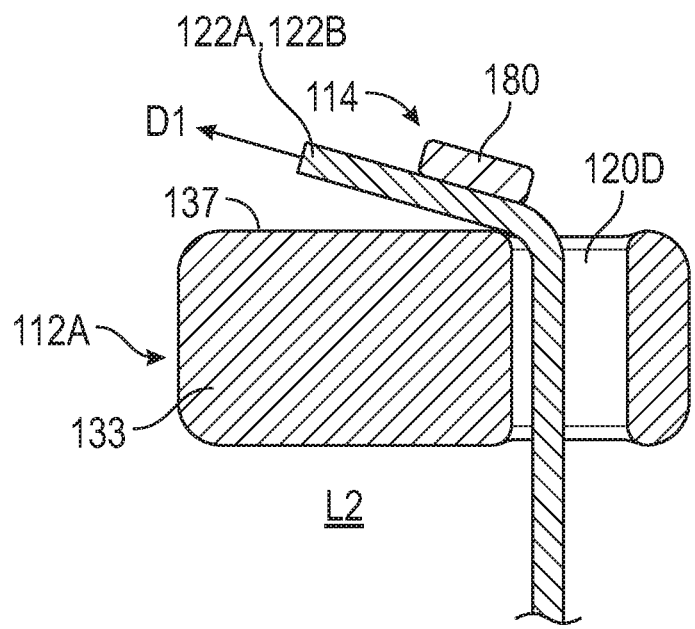
FIGS. 24A and 24B illustrate an unlocked position of a locking mechanism of a surgical fixation system.
Figure 24B:
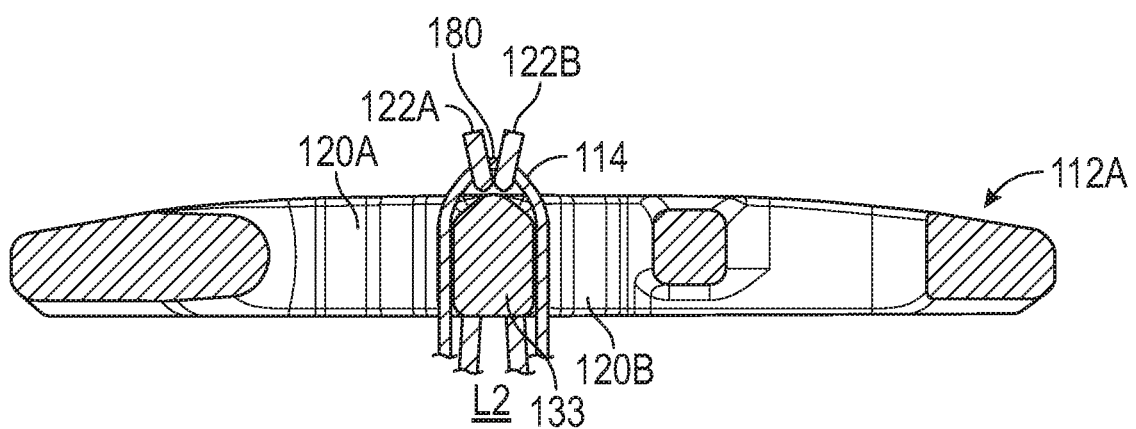
Figure 25:
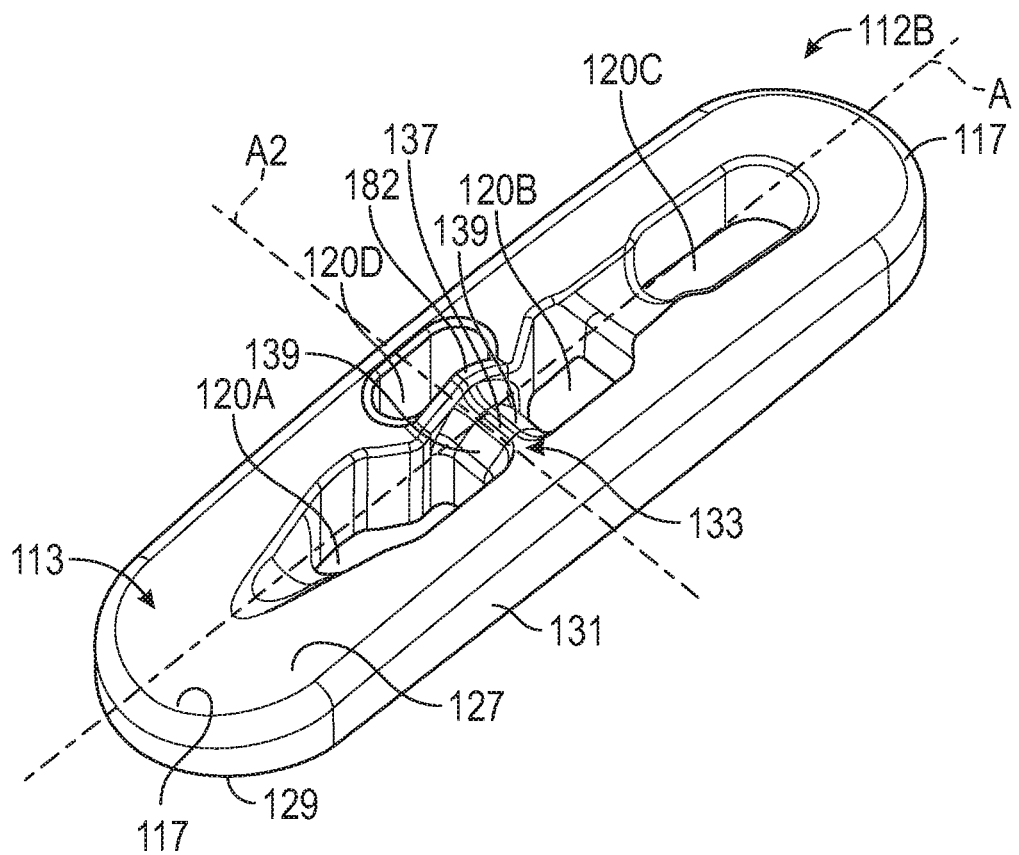
FIG. 25 illustrates another exemplary fixation device that can be used with the surgical fixation system of FIG. 18.
Figure 26:
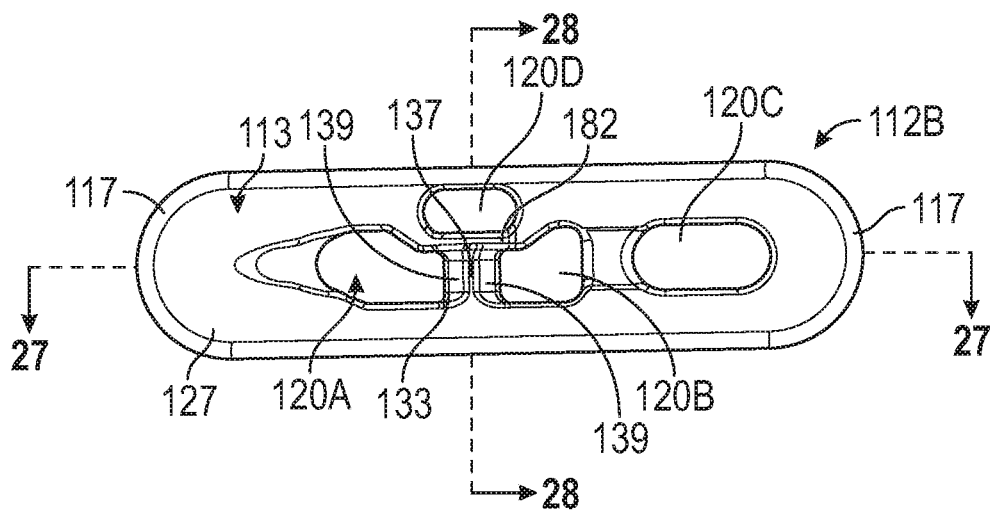
FIG. 26 is a top view of the fixation device of FIG. 25.
Figure 27:
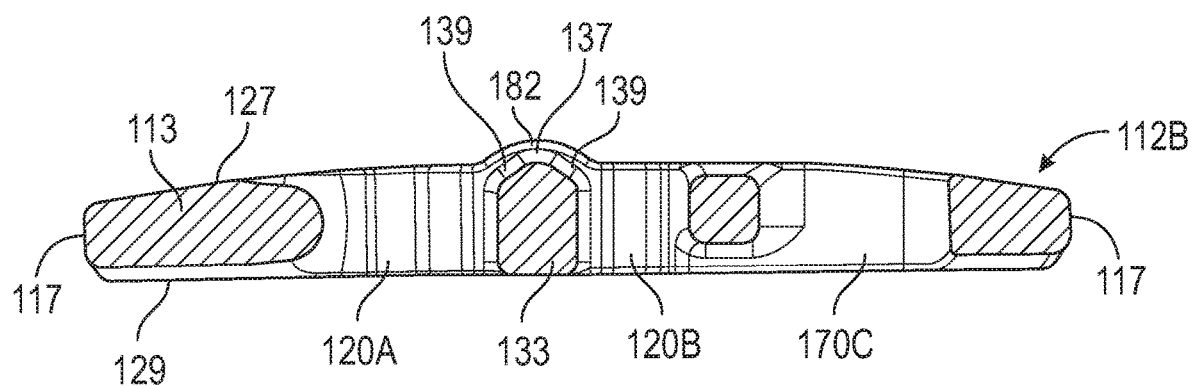
FIG. 27 is a cross-sectional view through section 27-27 of FIG. 26.
Figure 28:
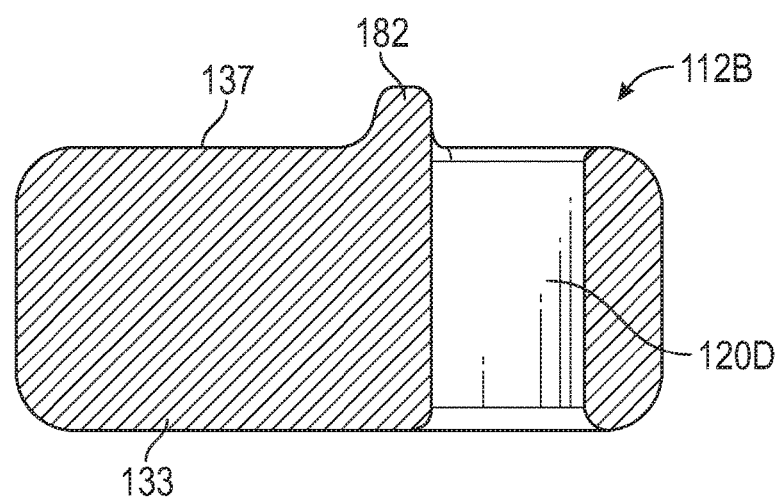
FIG. 28 is a cross-sectional view through section 28-28 of FIG. 26.

FIGS. 24A and 24B illustrate an unlocked position L2 of the locking mechanism 199 that is established by the loop 114 and the fixation device 112A. In the unlocked position L2, the tension that holds the loop section 180 against the free braid strands 122A and 122B is released, such as by releasing the tension on the graft 116, thereby permitting the free braid strands 122A, 122B to move relative to the bridge 133 and the loop section 180. Once the tension being applied by the loop section 180 has been removed, the free braid strands 122A, 122B can be tensioned in, for example, a direction D1 to constrict the size of the first and/or second adjustable eyesplice loops 124A, 124B of the loop 114.

mom FIGS. 25-28 illustrate another exemplary fixation device 112B for use with a surgical fixation system, such as the surgical fixation system 110 of FIG. 18, for example. The fixation device 112B includes a body 113 that extends along a central longitudinal axis A between opposing end portions 117. In an embodiment, the body 113 of the fixation device 112B is oblong shaped.

The body 113 includes a top surface 127 and a bottom surface 129 that each extend between the opposing end portions 117. A side wall 131 extends between the top surface 127 and the bottom surface 129. Together, the top surface 127, the bottom surface 129, and the side wall 131 establish the body 113 of the fixation device 112B.

In an embodiment, the top surface 127 is a convex surface that curves in a direction away from the bottom surface 129. In another embodiment, the bottom surface 129 is a flat surface.

For example, a first aperture 120A, a second aperture 120B, a third aperture 120C, and a fourth aperture 120D may be formed through the body 113 of the fixation device 112B and extend through both the top surface 127 and the bottom surface 129. In an embodiment, the first aperture 120A, the second aperture 120B, and the third aperture 120C are axially aligned and, for example, may be disposed along the central longitudinal axis A, and the fourth aperture 120D may be offset from the central longitudinal axis A, for example, in a direction toward the side wall 131. In an embodiment, the first aperture 120A and the second aperture 120B include irregular shapes, and the third aperture 120C and the fourth aperture 120D are oval shaped. However, the sizes and shapes of the apertures are not intended to limit this disclosure.

The first aperture 120A and the second aperture 120B may be arranged to receive the loop 114 of the surgical fixation system 110. A bridge 133 separates the first and second apertures 120A, 120B from one another and provides a surface for carrying the loop 14 of the surgical fixation system 10. The bridge 133 may include an outer surface 137 that is flush with the top surface 127 of the fixation device 112B (i.e., the outer surface 137 is not countersunk relative to the top surface 127) and, for example, a pair of angled surfaces 139 that extend transversely from the bridge 133 in a direction toward the bottom surface 129 of the fixation device 112. In an embodiment, the outer surface 137 of the bridge 33 extends along a longitudinal axis A2 that may be generally perpendicular to the central longitudinal axis A of the body 113 (see FIG. 25).

The third aperture 120C may be used to carry one or more filaments 115 for passing the fixation device 112B through a bone tunnel and/or for flipping the fixation device 112 relative to bone after exiting from the bone tunnel. The third aperture 120C may be, for example, the aperture that is closest to one of the opposing end portions 117 of the fixation device 112B.

The fourth aperture 120D may be utilized as a suture return aperture for receiving the free braid strands 122A, 122B of the loop 114. The fourth aperture 120D may be located adjacent to the first and second apertures 120A, 120B. In an embodiment, the longitudinal axis A2 extending through the outer surface 137 of the bridge 133 may intersect the fourth aperture 120D (see, e.g., FIG. 25).

A bump 182 may be positioned laterally between the bridge 133 and the fourth aperture 120D of the fixation device 112B. The bump 182 may protrude outwardly from the top surface 127 of the fixation device 112B and the outer surface 137 of the bridge 133. Unlike the outer surface 137 of the bridge 133 in this example, the bump 182 is therefore not flush relative to the top surface 127.

With reference to FIGS. 18 and 25-28, the fixation device 112B and the loop 114 may be configured to establish the locking mechanism 199 of the surgical fixation system 110. In an embodiment, a first free braid strand 122A extends from a first spliced section 172 of the loop 114, and a second free braid strand 122B extends from a second spliced section 174 of the loop 114. The first free braid strand 122A and the second free braid strand 122B may be passed upwardly through, as in this example, the fourth aperture 120D (i.e., for example, in a direction that extends from the bottom surface 129 toward the top surface 127 of the fixation device 112A), may then be passed along a tortuous path up and over the bump 182, and may then be passed beneath a loop section 180 of the loop 114 that may, for example, rest over the bridge 133 to establish the locking mechanism 199.

Figure 29A:
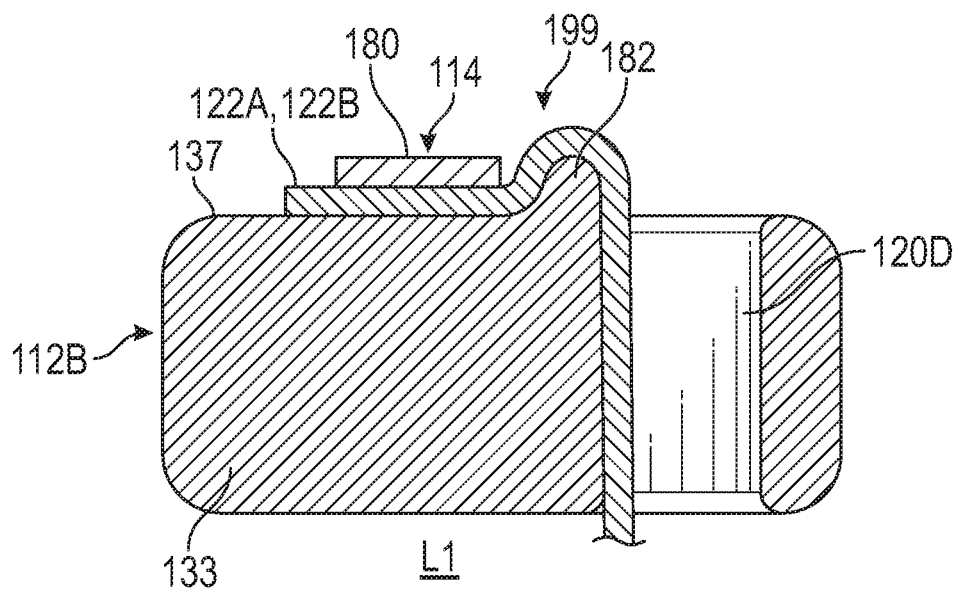
FIGS. 29A and 29B illustrate a locked position of a locking mechanism of a surgical fixation system.
Figure 29B:
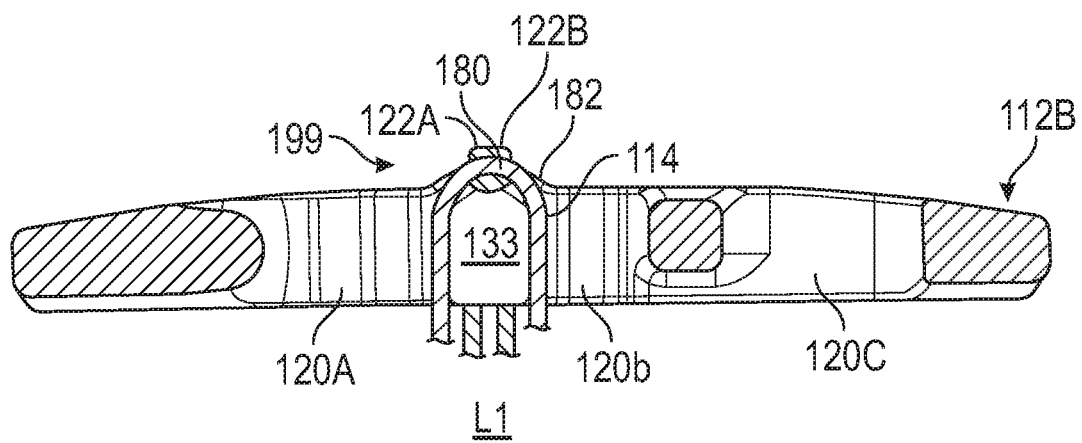

FIGS. 29A and 29B illustrate a locked position L1 of the locking mechanism 199 that may be established by the loop 114 and the fixation device 112B. In the locked position L1, the free braid strands 122A and 122B are held in tension directly against the outer surface 137 of the bridge 133 by the loop section 180 of the loop 114. This tension may be created, for example, by tensioning an opposite section of the loop 114 (i.e., for example, the section that carries the graft 116). The bump 182 of the fixation device 112B may augment the amount of tension that can be exerted against the free braid strands 122A, 122B in the locked position L1. The free braid strands 122A, 122B are therefore held against the type of movement that is necessary for constricting the size of the first and second adjustable eyesplice loops 124A, 124B of the loop 114.

Figure 30A:
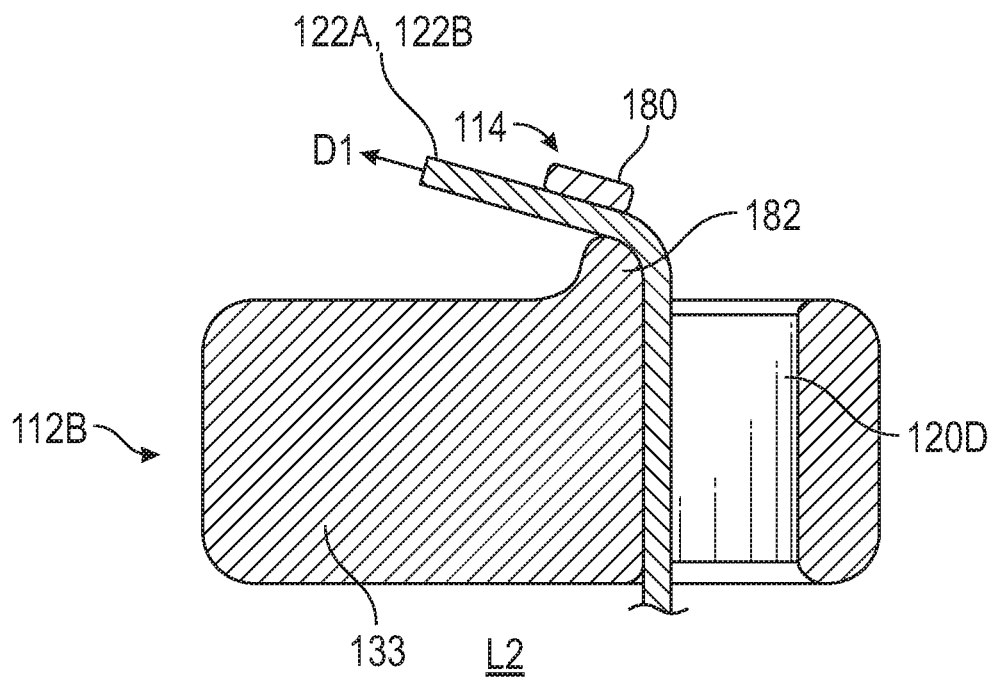
FIGS. 30A and 30B illustrate an unlocked position of a locking mechanism of a surgical fixation system.
Figure 30B:
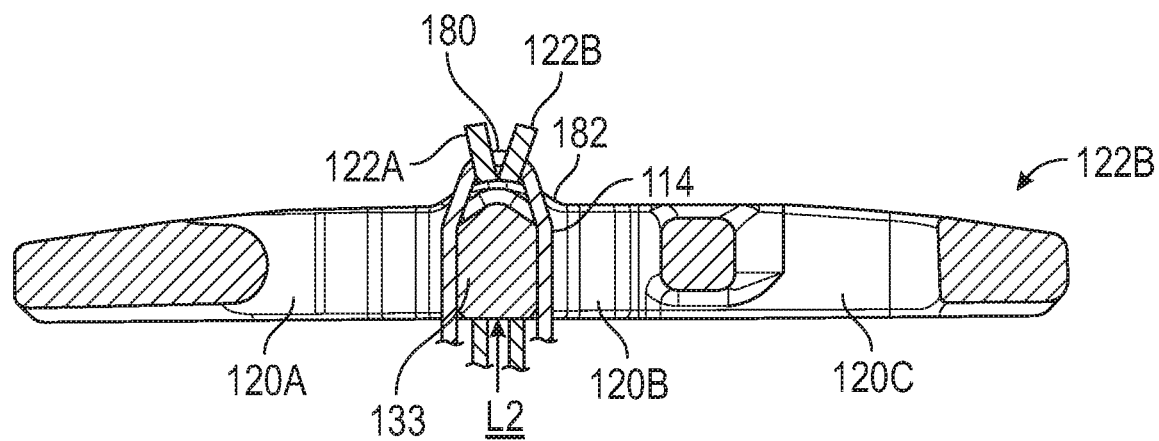

FIGS. 30A and 30B illustrate an unlocked position L2 of the locking mechanism 199 that is established by the loop 114 and the fixation device 112B. In the unlocked position L2, the tension that holds the loop section 180 against the free braid strands 122A and 122B is released, such as by releasing the tension on the graft 116, thereby permitting the free braid strands 122A, 122B to move relative to the bridge 133, the loop section 180, and the bump 182. Once the tension being applied by the loop section 180 has been removed, the free braid strands 122A, 122B can be tensioned in a direction D1 to constrict the size of the first and/or second adjustable eyesplice loops 124A, 124B of the loop 114.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A surgical fixation system, comprising:
   a fixation device including a body that extends along a central longitudinal axis and includes a top surface and a bottom surface;
   a first aperture, a second aperture, and a suture return aperture that each extend through the body;
   a bridge extending between the first aperture and the second aperture;
   an adjustable loop connected to the first aperture and the second aperture;
   a first free braid strand extending from a first spliced section of the adjustable loop;
   a second free braid strand extending from a second spliced section of the adjustable loop; and
   the first free braid strand and the second free braid strand extending through the suture return aperture and then under a loop section of the adjustable loop that rests over the bridge to establish a locking mechanism of the surgical fixation system;
   wherein, in a locked position of the locking mechanism, the first free braid strand and the second free braid strand are tensioned against an outer surface of the bridge by the loop section of the adjustable loop, wherein the first free braid strand extends from the first spliced section and then through the suture return aperture without passing through either the first aperture or the second aperture.

2. The system as recited in claim 1, wherein the outer surface of the bridge is flush with the top surface of the fixation device.

3. The system as recited in claim 1, wherein a longitudinal axis extending through the outer surface of the bridge is perpendicular to the central longitudinal axis.

4. The system as recited in claim 3, wherein the longitudinal axis extending through the outer surface of the bridge intersects the suture return aperture.

5. The system as recited in claim 4, wherein the longitudinal axis of the bridge intersects across a width of the suture return aperture, wherein the width is transverse to a longitudinal axis of the suture return aperture.

6. The system as recited in claim 1, wherein the first aperture and the second aperture are axially aligned and are disposed along the central longitudinal axis, and the suture return aperture is offset from the central longitudinal axis in a direction toward a side wall of the body.

7. The system as recited in claim 1, comprising a bump that protrudes outwardly from the top surface at a location adjacent to the suture return aperture, and wherein the first free braid strand and the second free braid strand extend up and over the bump.

8. The system as recited in claim 1, wherein the second free braid strand extends from the second spliced section and then through the suture return aperture without passing through either the first aperture or the second aperture.

9. The system as recited in claim 1, wherein the first aperture and the second aperture include irregular shapes, and the suture return aperture is oval shaped.

10. The system as recited in claim 1, wherein the top surface is a convex surface, and the bottom surface is a flat surface.

11. A surgical fixation system, comprising:
a fixation device including a body that extends along a central longitudinal axis and includes a top surface and a bottom surface;
a first aperture, a second aperture, and a suture return aperture that each extend through the body;
a bridge extending between the first aperture and the second aperture;
an adjustable loop connected to the first aperture and the second aperture;
a first free braid strand extending from a first spliced section of the adjustable loop;
a second free braid strand extending from a second spliced section of the adjustable loop;
the first free braid strand and the second free braid strand extending through the suture return aperture and then under a loop section of the adjustable loop that rests over the bridge to establish a locking mechanism of the surgical fixation system;
wherein, in a locked position of the locking mechanism, the first free braid strand and the second free braid strand are tensioned against an outer surface of the bridge by the loop section of the adjustable loop; and
a bump disposed laterally between the suture return aperture and the bridge.

12. The system as recited in claim 11, wherein, in the locked position of the locking mechanism, the first free braid strand and the second free braid strand are tensioned against the bump.

13. A surgical fixation system, comprising:
a fixation device including a body that extends along a central longitudinal axis between opposing end portions, wherein the body includes a top surface and a bottom surface;
a first aperture, a second aperture, and a suture return aperture that each extend through the body;
a bridge extending between the first aperture and the second aperture;
an adjustable loop connected to the first aperture and the second aperture;
a first free braid strand extending from a first spliced section of the adjustable loop;
a second free braid strand extending from a second spliced section of the adjustable loop; and
the first free braid strand and the second free braid strand extending through the suture return aperture and then under a loop section of the adjustable loop that rests over the bridge to establish a locking mechanism of the surgical fixation system;
wherein, in a locked position of the locking mechanism, the first free braid strand and the second free braid strand are tensioned against an outer surface of the bridge by the loop section of the adjustable loop,
wherein the first free braid strand extends directly from the first spliced section through the suture return aperture,
wherein the first aperture and the second aperture are axially aligned and are disposed along the central longitudinal axis, and the suture return aperture is offset from the central longitudinal axis in a direction toward a side wall of the body.

* * * * *